US009644026B2

(12) United States Patent
Shinagawa et al.

(10) Patent No.: US 9,644,026 B2
(45) Date of Patent: May 9, 2017

(54) ANTIBODY AGAINST MUTANT α-ACTININ-4

(75) Inventors: Shingo Shinagawa, Kobe (JP); Kazunari Ito, Kobe (JP); Yoshimi Tokashiki, Kobe (JP); Tomoaki Miyamoto, Kobe (JP); Kazufumi Honda, Tokyo (JP); Tesshi Yamada, Tokyo (JP)

(73) Assignees: TRANS GENIC INC., Fukuoka-Shi (JP); NATIONAL CANCER CENTER, Tokyo (JP)

( * ) Notice: Subject to any disclaimer, the term of this patent is extended or adjusted under 35 U.S.C. 154(b) by 181 days.

(21) Appl. No.: 14/343,221

(22) PCT Filed: Sep. 9, 2011

(86) PCT No.: PCT/JP2011/071168
§ 371 (c)(1),
(2), (4) Date: Mar. 6, 2014

(87) PCT Pub. No.: WO2013/035208
PCT Pub. Date: Mar. 14, 2013

(65) Prior Publication Data
US 2014/0248261 A1 Sep. 4, 2014

(51) Int. Cl.
| | |
|---|---|
| *C07K 16/18* | (2006.01) |
| *C07K 16/30* | (2006.01) |
| *C12N 15/113* | (2010.01) |
| *C12N 5/16* | (2006.01) |
| *G01N 33/574* | (2006.01) |

(52) U.S. Cl.
CPC .......... *C07K 16/18* (2013.01); *C07K 16/3069* (2013.01); *C12N 5/163* (2013.01); *C12N 15/113* (2013.01); *G01N 33/57496* (2013.01); *C07K 2317/34* (2013.01); *C12N 2310/14* (2013.01)

(58) Field of Classification Search
None
See application file for complete search history.

(56) References Cited

U.S. PATENT DOCUMENTS

| | | | |
|---|---|---|---|
| 7,521,195 B1 | 4/2009 | Joseloff et al. | |
| 2003/0077292 A1* | 4/2003 | Hanash .............. | A61K 39/0011 424/185.1 |
| 2006/0236417 A1* | 10/2006 | Sakaguchi ......... | A01K 67/0275 800/18 |
| 2009/0232822 A1 | 9/2009 | Joseloff et al. | |
| 2011/0212085 A1 | 9/2011 | Joseloff et al. | |

OTHER PUBLICATIONS

Weins et al. (PNAS, 104(41): 16080-16085, 2007).*
Mariuzza et al. (Annu. Rev. Biophys. Biophys. Chem. 1987; 16: 139-159).*
Extended European Search Report dated Dec. 18, 2014, for European Application No. 11872034.1.
Menez et al., "Mutant [alpha]-actinin-4 promotes tumorigenicity and regulates cell motility of a human lung carcinoma", Oncogene, vol. 23, 2004, pp. 2630-2639.
Weins et al., "Disease-associated mutant [alpha]-actinin-4 reveals a mechanism for regulating its F-actin-binding affinity", PNAS, vol. 104, No. 41, Oct. 9, 2007, pp. 16080-16085.
Beggs et al., "Cloning and Characterization of Two Human Skeletal Muscle α-Actinin Genes Located on Chromosomes1 and 11*," The Journal of Biological Chemistry, vol. 267, No. 13, pp. 9281-9288, May 5, 1992.
Honda et al., "Actinin-4, a Novel Actin-bundling Protein Associated with Cell Motility and Cancer Invasion," The Journal of Cell Biology, vol. 140, No. 6, Mar. 23, 1998 (downloaded from jcp.rupress.org on Feb. 24, 2014), pp. 1383-1393.
Honda et al., "Alternative splice variant of actinin-4 in small cell lung cancer," Oncogene, vol. 23, 2004 (Published online: May 3, 2004), pp. 5257-5262.
Honda, "Biological functions of actin-binding protein, actinin-4, in cancer metastasis and invasion," The Journal of Japanese Biochemical Society, vol. 79, No. 7, Jul. 25, 2007, pp. 643-654, with English translation.
Horoshima et al., "Distinction of pulmonary large cell neuroendocrine carcinoma from small cell lung carcinoma: a morphological, immunohistochemical, and molecular analysis," Modern Pathology, vol. 19, 2006 (published online: Jul. 7, 2006), pp. 1358-1368.
International Search Report dated Dec. 13, 2011 for International Application No. PCT/JP2011/071168.
Ionescu et al., "Nonsmall Cell Lung Carcinoma With Neuroendocrine Differentiation—An Entity of No Clinical or Prognostic Significance," American Journal of Surgical Pathology, vol. 31, No. 1, Jan. 2007, pp. 26-32.
Otey et al., "α-Actinin Revisited: A Fresh Look at an Old Player," Cell Motility and the Cytoskeleton, vol. 58, 2004,pp. 104-111.
Youssoufian et al., "Cloning and Chromosomal Localization of the Human Cytoskeletal a-Actinin Gene Reveals Linkage to the β-Spectrin Gene," The American Journal of Human Genetics, vol. 47, 1990, pp. 62-72.
European Office Action, dated Jan. 21, 2016, for European Application No. 11872034.1.
Miyanaga et al., "Diagnostic and prognostic significance of the alternatively spliced ACTN4 variant in high-grade neuroendocrine pulmonary tumours," Annals of Oncology Advance Access, vol. 24, No. 1, Aug. 10, 2012, pp. 1-7.
Ono et al., "Prolyl 4-Hydroxylation of α-Fibrinogen; A Novel Protein Modification Revealed by Plasma Proteomics," The Journal of Biological Chemistry, vol. 284, No. 42, Oct. 16, 2009, pp. 29041-29049.

* cited by examiner

*Primary Examiner* — Brad Duffy
*Assistant Examiner* — Nelson B Moseley, II
(74) *Attorney, Agent, or Firm* — Birch, Stewart, Kolasch & Birch, LLP

(57) ABSTRACT

An antibody against mutant α-actinin-4 having an amino acid sequence with at least one amino acid residue substitution in the region between position 245 and 263 in the amino acid sequence of α-actinin-4, wherein the antibody recognizes all or a part of the substituted amino acid residue(s) in the region.

17 Claims, 8 Drawing Sheets
(4 of 8 Drawing Sheet(s) Filed in Color)

Confirmation testing for purified antibody titer against each antigen
13G9

Confirmation testing for purified antibody titer against each antigen
11H2

Confirmation testing for purified antibody titer against each antigen
9B3

Confirmation testing for purified antibody titer against each antigen
15H2

Confirmation testing for purified antibody titer against each antigen
10E10

SEQUENCE LISTING

```
<160> NUMBER OF SEQ ID NOS: 12

<210> SEQ ID NO 1
<211> LENGTH: 3966
<212> TYPE: DNA
<213> ORGANISM: Homo sapiens
<220> FEATURE:
<221> NAME/KEY: CDS
<222> LOCATION: (120)..(2855)

<400> SEQUENCE: 1
aggcgcgggc ggagggcggg ctgaagcagc tgaagcggcg gtagcggcgg cggctcgggc    60
agaggggcgg gagctgaggc gggagcggac aggctggtgg gcgagcgaga ggcggcgga   119 atg gtg gac tac cac gcg gcg aac cag tcg tac cag tac ggc ccc agc    167
Met Val Asp Tyr His Ala Ala Asn Gln Ser Tyr Gln Tyr Gly Pro Ser
1               5                   10                  15 agc gcg ggc aat ggc gct ggc ggc ggg ggc agc atg ggc gac tac atg    215
Ser Ala Gly Asn Gly Ala Gly Gly Gly Gly Ser Met Gly Asp Tyr Met
                20                  25                  30 gcc cag gag gac gac tgg gac cgg gac ctg ctg ctg gac ccg gcc tgg    263
Ala Gln Glu Asp Asp Trp Asp Arg Asp Leu Leu Leu Asp Pro Ala Trp
            35                  40                  45 gag aag cag cag cgc aag acc ttc acg gca tgg tgc aac tcc cac ctg    311
Glu Lys Gln Gln Arg Lys Thr Phe Thr Ala Trp Cys Asn Ser His Leu
        50                  55                  60 cgg aag gca ggc aca cag atc gag aac att gat gag gac ttc cga gac    359
Arg Lys Ala Gly Thr Gln Ile Glu Asn Ile Asp Glu Asp Phe Arg Asp
65                  70                  75                  80 ggg ctc aag ctc atg ctc ctg gag gtc ata tca ggg gag cgg tta        407
Gly Leu Lys Leu Met Leu Leu Glu Val Ile Ser Gly Glu Arg Leu
                85                  90                  95 cct aag ccg gag cgg ggg aag atg aga gtg cac aaa atc aac aat gtg    455
Pro Lys Pro Glu Arg Gly Lys Met Arg Val His Lys Ile Asn Asn Val
                100                 105                 110 aac aaa gcg ctg gac ttt att gcc agc aaa ggc gtc aag ctg gtc tcc    503
Asn Lys Ala Leu Asp Phe Ile Ala Ser Lys Gly Val Lys Leu Val Ser
            115                 120                 125 atc ggg gca gaa gag att gtg gac ggc aac gca aag atg acc ctg gga    551
Ile Gly Ala Glu Glu Ile Val Asp Gly Asn Ala Lys Met Thr Leu Gly
        130                 135                 140
```

-continued

| | |
|---|---|
| atg atc tgg acc atc atc ctt agg ttc gcc atc cag gac atc tcc gtg<br>Met Ile Trp Thr Ile Ile Leu Arg Phe Ala Ile Gln Asp Ile Ser Val<br>145                          150                    155                    160 | 599 |
| gaa gag acc tcg gcc aag gaa ggg ctc ctt ctc tgg tgc cag aga aag<br>Glu Glu Thr Ser Ala Lys Glu Gly Leu Leu Leu Trp Cys Gln Arg Lys<br>                 165                    170                    175 | 647 |
| aca gcc ccg tat aag aac gtc aat gtg cag aac ttc cac atc agc tgg<br>Thr Ala Pro Tyr Lys Asn Val Asn Val Gln Asn Phe His Ile Ser Trp<br>                    180                    185                    190 | 695 |
| aag gat ggt ctt gcc ttc aat gcc ctg atc cac cgg cac aga cca gag<br>Lys Asp Gly Leu Ala Phe Asn Ala Leu Ile His Arg His Arg Pro Glu<br>          195                    200                    205 | 743 |
| ctg att gag tat gac aag ctg agg aag gac gac cct gtc acc aac ctg<br>Leu Ile Glu Tyr Asp Lys Leu Arg Lys Asp Asp Pro Val Thr Asn Leu<br>210                          215                    220 | 791 |
| aac aat gcc ttc gaa gtg gct gag aaa tac ctc gac atc ccc aag atg<br>Asn Asn Ala Phe Glu Val Ala Glu Lys Tyr Leu Asp Ile Pro Lys Met<br>225                          230                    235                    240 | 839 |
| ctg gat gca gag gac atc gtg aac acg gcc cgg ccc gac gag aag gcc<br>Leu Asp Ala Glu Asp Ile Val Asn Thr Ala Arg Pro Asp Glu Lys Ala<br>                        245                    250                    255 | 887 |
| ata atg acc tat gtg tcc agc ttc tac cat gcc ttt tca gga gcg cag<br>Ile Met Thr Tyr Val Ser Ser Phe Tyr His Ala Phe Ser Gly Ala Gln<br>                    260                    265                    270 | 935 |
| aag gct gaa act gcc gcc aac cgg atc tgt aag gtg ctg gct gtc aac<br>Lys Ala Glu Thr Ala Ala Asn Arg Ile Cys Lys Val Leu Ala Val Asn<br>          275                    280                    285 | 983 |
| caa gag aac gag cac ctg atg gag gac tac gag aag ctg gcc agc gac<br>Gln Glu Asn Glu His Leu Met Glu Asp Tyr Glu Lys Leu Ala Ser Asp<br>290                          295                    300 | 1031 |
| ctc ctg gag tgg atc cgg cgc acc atc ccc tgg ctg gag gac cgt gtg<br>Leu Leu Glu Trp Ile Arg Arg Thr Ile Pro Trp Leu Glu Asp Arg Val<br>305                          310                    315                    320 | 1079 |
| ccc caa aag act atc cag gag atg cag cag aag ctg gag gac ttc cgc<br>Pro Gln Lys Thr Ile Gln Glu Met Gln Gln Lys Leu Glu Asp Phe Arg<br>                        325                    330                    335 | 1127 |
| gac tac cgg cgt gtg cac aag ccg ccc aag gtg cag gag aag tgc cag<br>Asp Tyr Arg Arg Val His Lys Pro Pro Lys Val Gln Glu Lys Cys Gln<br>                    340                    345                    350 | 1175 |
| ctg gag atc aac ttc aac acg ctg cag acc aag ctg cgc ctc agc aac<br>Leu Glu Ile Asn Phe Asn Thr Leu Gln Thr Lys Leu Arg Leu Ser Asn<br>          355                    360                    365 | 1223 |
| cgg ccc gcc ttc atg ccc tcc gag ggc aag atg gtc tcg gac atc aac<br>Arg Pro Ala Phe Met Pro Ser Glu Gly Lys Met Val Ser Asp Ile Asn<br>370                          375                    380 | 1271 |
| aat ggc tgg cag cac ttg gag cag gct gag aag ggc tac gag gag tgg<br>Asn Gly Trp Gln His Leu Glu Gln Ala Glu Lys Gly Tyr Glu Glu Trp<br>385                          390                    395                    400 | 1319 |
| ctg ctg aat gag atc cgc agg ctg gag cgg ctc gac cac ctg gca gag<br>Leu Leu Asn Glu Ile Arg Arg Leu Glu Arg Leu Asp His Leu Ala Glu<br>                        405                    410                    415 | 1367 |
| aag ttc cgg cag aag gcc tcc atc cac gag gcc tgg act gac ggg aag<br>Lys Phe Arg Gln Lys Ala Ser Ile His Glu Ala Trp Thr Asp Gly Lys<br>                    420                    425                    430 | 1415 |
| gaa gcc atg ctg aag cac cgg gac tac gag acg gcc aca cta tcg gac<br>Glu Ala Met Leu Lys His Arg Asp Tyr Glu Thr Ala Thr Leu Ser Asp<br>          435                    440                    445 | 1463 |
| atc aaa gcc ctc att cgc aag cac gag gcc ttc gag agc gac ctg gct<br>Ile Lys Ala Leu Ile Arg Lys His Glu Ala Phe Glu Ser Asp Leu Ala<br>450                          455                    460 | 1511 |

-continued

| | | |
|---|---|---|
| gcg cac cag gac cgc gtg gag cag atc gcc gcc att gcc cag gag ctc<br>Ala His Gln Asp Arg Val Glu Gln Ile Ala Ala Ile Ala Gln Glu Leu<br>465                       470                  475                  480 | 1559 |
| aac gag ctg gat tac tac gac tcc cac aat gtc aac acc cgg tgc cag<br>Asn Glu Leu Asp Tyr Tyr Asp Ser His Asn Val Asn Thr Arg Cys Gln<br>                        485                  490                 495 | 1607 |
| aag atc tgt gac cag tgg gac gcc ctc ggc tct ctg aca cat agt cgc<br>Lys Ile Cys Asp Gln Trp Asp Ala Leu Gly Ser Leu Thr His Ser Arg<br>              500                  505                  510 | 1655 |
| agg gaa gcc ctg gag aaa aca gag aag cag ctg gag gcc atc gac cag<br>Arg Glu Ala Leu Glu Lys Thr Glu Lys Gln Leu Glu Ala Ile Asp Gln<br>515                       520                  525 | 1703 |
| ctg cac ctg gaa tac gcc aag cgc gcg gcc ccc ttc aac aac tgg atg<br>Leu His Leu Glu Tyr Ala Lys Arg Ala Ala Pro Phe Asn Asn Trp Met<br>      530                  535                  540 | 1751 |
| gag agc gcc atg gag gac ctc cag gac atg ttc atc gtc cat acc atc<br>Glu Ser Ala Met Glu Asp Leu Gln Asp Met Phe Ile Val His Thr Ile<br>545                       550                  555                 560 | 1799 |
| gag gag att gag ggc ctg atc tca gcc cat gac cag ttc aag tcc acc<br>Glu Glu Ile Glu Gly Leu Ile Ser Ala His Asp Gln Phe Lys Ser Thr<br>                       565                  570                575 | 1847 |
| ctg ccg gac gcc gat agg gag cgc gag gcc atc ctg gcc atc cac aag<br>Leu Pro Asp Ala Asp Arg Glu Arg Glu Ala Ile Leu Ala Ile His Lys<br>              580                  585                  590 | 1895 |
| gag gcc cag agg atc gct gag agc aac cac atc aag ctg tcg ggc agc<br>Glu Ala Gln Arg Ile Ala Glu Ser Asn His Ile Lys Leu Ser Gly Ser<br>595                       600                  605 | 1943 |
| aac ccc tac acc acc gtc acc ccg caa atc atc aac tcc aag tgg gag<br>Asn Pro Tyr Thr Thr Val Thr Pro Gln Ile Ile Asn Ser Lys Trp Glu<br>      610                  615                  620 | 1991 |
| aag gtg cag cag ctg gtg cca aaa cgg gac cat gcc ctc ctg gag gag<br>Lys Val Gln Gln Leu Val Pro Lys Arg Asp His Ala Leu Leu Glu Glu<br>625                       630                  635                640 | 2039 |
| cag agc aag cag cag tcc aac gag cac ctg cgc cgc cag ttc gcc agc<br>Gln Ser Lys Gln Gln Ser Asn Glu His Leu Arg Arg Gln Phe Ala Ser<br>                       645                  650                655 | 2087 |
| cag gcc aat gtt gtg ggg ccc tgg atc cag acc aag atg gag gag atc<br>Gln Ala Asn Val Val Gly Pro Trp Ile Gln Thr Lys Met Glu Glu Ile<br>              660                  665                  670 | 2135 |
| ggg cgc atc tcc att gag atg aac ggg acc ctg gag gac cag ctg agc<br>Gly Arg Ile Ser Ile Glu Met Asn Gly Thr Leu Glu Asp Gln Leu Ser<br>675                       680                  685 | 2183 |
| cac ctg aag cag tat gaa cgc agc atc gtg gac tac aag ccc aac ctg<br>His Leu Lys Gln Tyr Glu Arg Ser Ile Val Asp Tyr Lys Pro Asn Leu<br>      690                  695                  700 | 2231 |
| gac ctg ctg gag cag cag cac cag ctc atc cag gag gcc ctc atc ttc<br>Asp Leu Leu Glu Gln Gln His Gln Leu Ile Gln Glu Ala Leu Ile Phe<br>705                       710                  715                720 | 2279 |
| gac aac aag cac acc aac tat acc atg gag cac atc cgc gtg ggc tgg<br>Asp Asn Lys His Thr Asn Tyr Thr Met Glu His Ile Arg Val Gly Trp<br>                       725                  730                735 | 2327 |
| gag cag ctg ctc acc acc att gcc cgc acc atc aac gag gtg gag aac<br>Glu Gln Leu Leu Thr Thr Ile Ala Arg Thr Ile Asn Glu Val Glu Asn<br>              740                  745                  750 | 2375 |
| cag atc ctc acc cgc gac gcc aag ggc atc agc cag gag cag atg cag<br>Gln Ile Leu Thr Arg Asp Ala Lys Gly Ile Ser Gln Glu Gln Met Gln<br>755                       760                  765 | 2423 |
| gag ttc cgg gcg tcc ttc aac cac ttc gac aag gat cat ggc ggg gcg<br>Glu Phe Arg Ala Ser Phe Asn His Phe Asp Lys Asp His Gly Gly Ala | 2471 |

```
                 770                 775                 780
ctg ggg ccc gag gag ttc aag gcc tgc ctc atc agc ctg ggc tac gac      2519
Leu Gly Pro Glu Glu Phe Lys Ala Cys Leu Ile Ser Leu Gly Tyr Asp
785                 790                 795                 800 gtg gag aac gac cgg cag ggt gag gcc gag ttc aac cgc atc atg agc      2567
Val Glu Asn Asp Arg Gln Gly Glu Ala Glu Phe Asn Arg Ile Met Ser
                805                 810                 815 ctg gtc gac ccc aac cat agc ggc ctt gtg acc ttc caa gcc ttc atc      2615
Leu Val Asp Pro Asn His Ser Gly Leu Val Thr Phe Gln Ala Phe Ile
            820                 825                 830 gac ttc atg tcg cgg gag acc acc gac acg gac acg gct gac cag gtc      2663
Asp Phe Met Ser Arg Glu Thr Thr Asp Thr Asp Thr Ala Asp Gln Val
        835                 840                 845 atc gct tcc ttc aag gtc tta gca ggg gac aag aac ttc atc aca gct      2711
Ile Ala Ser Phe Lys Val Leu Ala Gly Asp Lys Asn Phe Ile Thr Ala
    850                 855                 860 gag gag ctg cgg aga gag ctg ccc ccc gac cag gcc gag tac tgc atc      2759
Glu Glu Leu Arg Arg Glu Leu Pro Pro Asp Gln Ala Glu Tyr Cys Ile
865                 870                 875                 880 gcc cgc atg gcg cca tac cag ggc cct gac gcc gtg ccc ggt gcc ctc      2807
Ala Arg Met Ala Pro Tyr Gln Gly Pro Asp Ala Val Pro Gly Ala Leu
                885                 890                 895 gac tac aag tcc ttc tcc acg gcc ttg tat ggc gag agc gac ctg tga      2855
Asp Tyr Lys Ser Phe Ser Thr Ala Leu Tyr Gly Glu Ser Asp Leu
            900                 905                 910 ggccccagag acctgaccca acaccccga cggcctccag gagggcctg ggcagcccca      2915 cagtcccatt cctccactct gtatctatgc aaagcactct ctgcagtcct ccggggtggg      2975
tgggtgggca gggaggggct ggggcaggct ctctcctctc tctctttgtg ggttggccag      3035
gaggttcccc cgaccaggtt ggggagactt ggggccagcg cttctggtct ggtaaatatg      3095
tatgatgtgt tgtgcttttt taaccaagga ggggccagtg gattcccaca gcacaaccgg      3155
tcccttccat gccctgggat gcctcaccac acccaggtct cttcctttgc tctgaggtcc      3215
cttcaaggcc tccccaatcc aggccaaagc ccatgtgcc ttgtccagga actgcctggg      3275
ccatgcgagg ggccagcaga gggcgccacc accacctgac ggctggggac ccacccagcc      3335
cctctcccct ctctgctcca gactcacttg ccattgccag gagatggccc caacaagcac      3395
cccgcttttg cagcagagga gctgagttgg cagaccgggc cccctgaac cgcacccat      3455 cccaccagcc ccggccttgc tttgtctggc ctcacgtgtc tcagattttc taagaaccaa      3515
aaaaaaaaaa ggaaaaaaaa cacaaaacaa caaaaaccaa aaaaaaaaa aatcacaaaa      3575 acaaaaaaac tataaaaaag aaagaattaa aaactttcag agaattacta tttactttat      3635
taacttacgg attttattata taaatatata ttcacctagc aacatatctc tgccgtctct      3695
cctgctctca taatgaagac atagccgatt ctctgcccgg gcccctttgct gatgctcctc      3755 cgggtctgcg tcgggcgtgg gtctctgggg accctccaga ggtggaggtg ggctgatggc      3815
ctggctgcct ggtggttgat ggttttgctc ccctaccctt ttttttttga gtttattctg      3875
attgattttt tttcttggtt tctggataaa ccaccctctg gggacaggat aataaaacat      3935
gtaatatttt taagaaggaa aaaaaaaaa a                                      3966

<210> SEQ ID NO 2
<211> LENGTH: 911
<212> TYPE: PRT
<213> ORGANISM: Homo sapiens

<400> SEQUENCE: 2
```

-continued

```
Met Val Asp Tyr His Ala Ala Asn Gln Ser Tyr Gln Tyr Gly Pro Ser
1               5                   10                  15

Ser Ala Gly Asn Gly Ala Gly Gly Gly Ser Met Gly Asp Tyr Met
            20                  25                  30

Ala Gln Glu Asp Trp Asp Arg Asp Leu Leu Leu Asp Pro Ala Trp
        35                  40                  45

Glu Lys Gln Gln Arg Lys Thr Phe Thr Ala Trp Cys Asn Ser His Leu
    50                  55                  60

Arg Lys Ala Gly Thr Gln Ile Glu Asn Ile Asp Glu Asp Phe Arg Asp
65                  70                  75                  80

Gly Leu Lys Leu Met Leu Leu Leu Glu Val Ile Ser Gly Glu Arg Leu
                85                  90                  95

Pro Lys Pro Glu Arg Gly Lys Met Arg Val His Lys Ile Asn Asn Val
            100                 105                 110

Asn Lys Ala Leu Asp Phe Ile Ala Ser Lys Gly Val Lys Leu Val Ser
        115                 120                 125

Ile Gly Ala Glu Glu Ile Val Asp Gly Asn Ala Lys Met Thr Leu Gly
    130                 135                 140

Met Ile Trp Thr Ile Ile Leu Arg Phe Ala Ile Gln Asp Ile Ser Val
145                 150                 155                 160

Glu Glu Thr Ser Ala Lys Glu Gly Leu Leu Leu Trp Cys Gln Arg Lys
                165                 170                 175

Thr Ala Pro Tyr Lys Asn Val Asn Val Gln Asn Phe His Ile Ser Trp
            180                 185                 190

Lys Asp Gly Leu Ala Phe Asn Ala Leu Ile His Arg His Arg Pro Glu
        195                 200                 205

Leu Ile Glu Tyr Asp Lys Leu Arg Lys Asp Asp Pro Val Thr Asn Leu
    210                 215                 220

Asn Asn Ala Phe Glu Val Ala Glu Lys Tyr Leu Asp Ile Pro Lys Met
225                 230                 235                 240

Leu Asp Ala Glu Asp Ile Val Asn Thr Ala Arg Pro Asp Glu Lys Ala
                245                 250                 255

Ile Met Thr Tyr Val Ser Ser Phe Tyr His Ala Phe Ser Gly Ala Gln
            260                 265                 270

Lys Ala Glu Thr Ala Ala Asn Arg Ile Cys Lys Val Leu Ala Val Asn
        275                 280                 285

Gln Glu Asn Glu His Leu Met Glu Asp Tyr Glu Lys Leu Ala Ser Asp
    290                 295                 300

Leu Leu Glu Trp Ile Arg Arg Thr Ile Pro Trp Leu Glu Asp Arg Val
305                 310                 315                 320

Pro Gln Lys Thr Ile Gln Glu Met Gln Gln Lys Leu Glu Asp Phe Arg
                325                 330                 335

Asp Tyr Arg Arg Val His Lys Pro Pro Lys Val Gln Glu Lys Cys Gln
            340                 345                 350

Leu Glu Ile Asn Phe Asn Thr Leu Gln Thr Lys Leu Arg Leu Ser Asn
        355                 360                 365

Arg Pro Ala Phe Met Pro Ser Glu Gly Lys Met Val Ser Asp Ile Asn
    370                 375                 380

Asn Gly Trp Gln His Leu Glu Gln Ala Glu Lys Gly Tyr Glu Glu Trp
385                 390                 395                 400

Leu Leu Asn Glu Ile Arg Arg Leu Glu Arg Leu Asp His Leu Ala Glu
                405                 410                 415
```

```
Lys Phe Arg Gln Lys Ala Ser Ile His Glu Ala Trp Thr Asp Gly Lys
                420                 425                 430

Glu Ala Met Leu Lys His Arg Asp Tyr Glu Thr Ala Thr Leu Ser Asp
            435                 440                 445

Ile Lys Ala Leu Ile Arg Lys His Glu Ala Phe Glu Ser Asp Leu Ala
        450                 455                 460

Ala His Gln Asp Arg Val Glu Gln Ile Ala Ala Ile Ala Gln Glu Leu
465                 470                 475                 480

Asn Glu Leu Asp Tyr Tyr Asp Ser His Asn Val Asn Thr Arg Cys Gln
                485                 490                 495

Lys Ile Cys Asp Gln Trp Asp Ala Leu Gly Ser Leu Thr His Ser Arg
                500                 505                 510

Arg Glu Ala Leu Glu Lys Thr Glu Lys Gln Leu Glu Ala Ile Asp Gln
                515                 520                 525

Leu His Leu Glu Tyr Ala Lys Arg Ala Ala Pro Phe Asn Asn Trp Met
        530                 535                 540

Glu Ser Ala Met Glu Asp Leu Gln Asp Met Phe Ile Val His Thr Ile
545                 550                 555                 560

Glu Glu Ile Glu Gly Leu Ile Ser Ala His Asp Gln Phe Lys Ser Thr
                565                 570                 575

Leu Pro Asp Ala Asp Arg Glu Arg Glu Ala Ile Leu Ala Ile His Lys
            580                 585                 590

Glu Ala Gln Arg Ile Ala Glu Ser Asn His Ile Lys Leu Ser Gly Ser
        595                 600                 605

Asn Pro Tyr Thr Thr Val Thr Pro Gln Ile Ile Asn Ser Lys Trp Glu
610                 615                 620

Lys Val Gln Gln Leu Val Pro Lys Arg Asp His Ala Leu Leu Glu Glu
625                 630                 635                 640

Gln Ser Lys Gln Gln Ser Asn Glu His Leu Arg Arg Gln Phe Ala Ser
                645                 650                 655

Gln Ala Asn Val Val Gly Pro Trp Ile Gln Thr Lys Met Glu Glu Ile
            660                 665                 670

Gly Arg Ile Ser Ile Glu Met Asn Gly Thr Leu Glu Asp Gln Leu Ser
        675                 680                 685

His Leu Lys Gln Tyr Glu Arg Ser Ile Val Asp Tyr Lys Pro Asn Leu
    690                 695                 700

Asp Leu Leu Glu Gln Gln His Gln Leu Ile Gln Glu Ala Leu Ile Phe
705                 710                 715                 720

Asp Asn Lys His Thr Asn Tyr Thr Met Glu His Ile Arg Val Gly Trp
                725                 730                 735

Glu Gln Leu Leu Thr Thr Ile Ala Arg Thr Ile Asn Glu Val Glu Asn
            740                 745                 750

Gln Ile Leu Thr Arg Asp Ala Lys Gly Ile Ser Gln Glu Gln Met Gln
        755                 760                 765

Glu Phe Arg Ala Ser Phe Asn His Phe Asp Lys Asp His Gly Gly Ala
    770                 775                 780

Leu Gly Pro Glu Glu Phe Lys Ala Cys Leu Ile Ser Leu Gly Tyr Asp
785                 790                 795                 800

Val Glu Asn Asp Arg Gln Gly Glu Ala Glu Phe Asn Arg Ile Met Ser
                805                 810                 815

Leu Val Asp Pro Asn His Ser Gly Leu Val Thr Phe Gln Ala Phe Ile
            820                 825                 830

Asp Phe Met Ser Arg Glu Thr Thr Asp Thr Asp Thr Ala Asp Gln Val
```

```
              835                 840                 845
Ile Ala Ser Phe Lys Val Leu Ala Gly Asp Lys Asn Phe Ile Thr Ala
        850                 855                 860
Glu Glu Leu Arg Arg Glu Leu Pro Pro Asp Gln Ala Glu Tyr Cys Ile
865                 870                 875                 880
Ala Arg Met Ala Pro Tyr Gln Gly Pro Asp Ala Val Pro Gly Ala Leu
                885                 890                 895
Asp Tyr Lys Ser Phe Ser Thr Ala Leu Tyr Gly Glu Ser Asp Leu
            900                 905                 910

<210> SEQ ID NO 3
<211> LENGTH: 19
<212> TYPE: PRT
<213> ORGANISM: Homo sapiens

<400> SEQUENCE: 3

Asp Ile Val Asn Thr Ala Arg Pro Asp Glu Lys Ala Ile Met Thr Tyr
1               5                  10                  15

Val Ser Ser

<210> SEQ ID NO 4
<211> LENGTH: 19
<212> TYPE: PRT
<213> ORGANISM: Homo sapiens

<400> SEQUENCE: 4

Asp Ile Val Gly Thr Leu Arg Pro Asp Glu Lys Ala Ile Met Thr Tyr
1               5                  10                  15

Val Ser Cys

<210> SEQ ID NO 5
<211> LENGTH: 22
<212> TYPE: DNA
<213> ORGANISM: Artificial
<220> FEATURE:
<223> OTHER INFORMATION: Synthetic DNA

<400> SEQUENCE: 5
ccgtataaga acgtcaatgt gc                                              22

<210> SEQ ID NO 6
<211> LENGTH: 20
<212> TYPE: DNA
<213> ORGANISM: Artificial
<220> FEATURE:
<223> OTHER INFORMATION: Synthetic DNA

<400> SEQUENCE: 6
ctggccagct tctcgtagtc                                                 20

<210> SEQ ID NO 7
<211> LENGTH: 17
<212> TYPE: DNA
<213> ORGANISM: Artificial
<220> FEATURE:
<223> OTHER INFORMATION: Synthetic DNA

<400> SEQUENCE: 7
tgggcactct gaggcca                                                    17

<210> SEQ ID NO 8
<211> LENGTH: 19
```

```
<212> TYPE: DNA
<213> ORGANISM: Artificial
<220> FEATURE:
<223> OTHER INFORMATION: Synthetic DNA

<400> SEQUENCE: 8
cttctgagcc cccgagaaa                                                19

<210> SEQ ID NO 9
<211> LENGTH: 16
<212> TYPE: DNA
<213> ORGANISM: Artificial
<220> FEATURE:
<223> OTHER INFORMATION: Synthetic DNA

<400> SEQUENCE: 9
tgagaaggcc atcatg                                                   16

<210> SEQ ID NO 10
<211> LENGTH: 19
<212> TYPE: RNA
<213> ORGANISM: Artificial
<220> FEATURE:
<223> OTHER INFORMATION: Synthetic RNA

<400> SEQUENCE: 10
ccaucaugac uuacguguc                                                19

<210> SEQ ID NO 11
<211> LENGTH: 19
<212> TYPE: RNA
<213> ORGANISM: Artificial
<220> FEATURE:
<223> OTHER INFORMATION: Synthetic RNA

<400> SEQUENCE: 11
uuacgugucc ugcuucuac                                                19

<210> SEQ ID NO 12
<211> LENGTH: 19
<212> TYPE: RNA
<213> ORGANISM: Artificial
<220> FEATURE:
<223> OTHER INFORMATION: Synthetic RNA

<400> SEQUENCE: 12
agaugagaag gccaucaug                                                19
```

ANTIBODY AGAINST MUTANT α-ACTININ-4

TECHNICAL FIELD

The present invention relates to an antibody against mutant α-actinin-4, more particularly a monoclonal antibody against a novel splice variant of α-actinin-4 protein.

BACKGROUND ART

α-Actinin-4 (hereinafter also referred to as ACTN4), which is a member of α-actinin, has a globular actin-binding domain at the N-terminal end and a calcium-binding motif (referred to as an EF-hand domain) at the C-terminal end. Moreover, ACTN4 forms dumbbell-shaped dimer through its central rod domain, and binds and bundles actin filaments with the actin-binding domain at each end (Non-patent Document 1). Mammalian α-actinin has been identified to have four isoforms, i.e., actinin-1 to actinin-4, wherein actinin-1 and actinin-4 are non-muscle isoforms, while actinin-2 and actinin-3 are muscle isoforms (Non-patent Documents 1, 2, 3 and 4).

ACTN4 is an actin-binding protein which is involved in actin bundling and promotes cell motility. It has been verified that ACTN4 is concentrated in cellular protrusions which appear to have enhanced cell motility. Further, it is suggested that ACTN4 may provide some positive contribution to cancer invasion (Non-patent Document 2).

In addition, a selective splice variant which skips exon 8 (where genetic mutations are found in families with familial focal glomerulosclerosis) and inserts novel (unknown) exon 8' is expressed specifically in small cell lung cancer, and its expression is verified only in testis among normal tissues; and hence it is suggested that this selective splice variant may be a cancer-testis antigen (Non-patent Document 5).

On the other hand, lung cancer is classified into two types, i.e., small cell lung cancer (hereinafter referred to as SCLC) and non-small cell lung cancer (hereinafter referred to as non-SCLC) by histological analysis. SCLC accounts for 20% of primary lung cancer and is often found in progressive form associated with multiple organ metastasis due to its high growth speed; and hence SCLC is known for "high malignancy" and "poor prognosis" (Non-patent Document 5).

In therapeutic aspects, SCLC requires different therapies from those for non-SCLC, most cases of which are adenocarcinoma and squamous cell carcinoma. For example, surgical therapies cannot be applied to SCLC even when it is in slightly advanced stage, while chemotherapies are less effective in non-SCLC cases. Because of these features, it has been considered that differentiation between SCLC and non-SCLC in an early stage is important for their appropriate treatment.

Moreover, large cell neuroendocrine carcinoma (hereinafter referred to as LCNEC), which is a subtype of large cell cancer included in non-SCLC, accounts for 3% of primary lung cancer and is known for "poor prognosis," as in the case of SCLC. LCNEC and SCLC are both high in neuroendocrine character, unlike other types of lung cancer (Non-patent Document 6).

Conventionally, SCLC and LCNEC have been collectively referred to as lung primary high-grade neuroendocrine tumor (HGNT), and, immunostaining utilizing neuroendocrine markers (chromogranin, synaptophysin, neural cell adhesion molecule (NCAM)) has been performed on excised specimens as one of their diagnostic techniques (Non-patent Document 7).

However, the positive rate of these three markers is far from being high, and their high false positive rate has been regarded as a problem. Thus, it is anticipated to develop a novel cancer marker which is highly specific to both small cell lung cancer and large cell neuroendocrine carcinoma and which allows early stage detection.

CITATION LIST

Non-patent Literature 1: Cell Motil. Cytoskeleton. 58, 104-111, 2004
Non-patent Literature 2: J. Cell Biol. 140, 1383-1393, 1998
Non-patent Literature 3: Am. J. Hum. Genet. 47, 62-71, 1990
Non-patent Literature 4: J. Biol. Chem. 267, 9281-9288, 1992
Non-patent Literature 5: Oncogene, 23, 5257-5262, 2004
Non-patent Literature 6: Mod Pathol. 19, 1358-68, 2006
Non-patent Literature 7: Am J Surg Pathol. 31, 26-32, 2007

SUMMARY OF THE INVENTION

Technical Problem

The present invention aims to provide an mutant ACTN4-specific monoclonal antibody which reacts with mutant ACTN4 (hereinafter referred to as ACTN4-Va), such as a novel splice variant protein of ACTN4, and does not react with constitutively expressed ACTN4 (hereinafter referred to as ACTN4-Ub), as well as a cell line producing such an antibody. The present invention also aims to provide a method for detecting the ACTN4-Va stated above and a detection reagent thereof and the like.

Solution to Problem

The inventors of the present invention have made extensive and intensive efforts to solve the problems stated above. By using ACTN4-Va or a polypeptide as an antigen, further using ACTN4-Ub or a polypeptide for screening purposes, and immunizing the antigen into a high-affinity antibody-producing transgenic non-human mammal, the inventors of the present invention have succeeded in obtaining an antibody which reacts with ACTN4-Va but not with ACTN4-Ub, i.e., a monoclonal antibody capable of distinguishing between ACTN4-Va and ACTN4-Ub. This finding led to the completion of the present invention.

Namely, the present invention is as follows.

(1) An antibody against mutant α-actinin-4 comprising an amino acid sequence with at least one amino acid residue substitution in the region between position 245 and 263 of α-actinin-4, wherein the antibody recognizes all or a part of the substituted amino acid residue(s) in the region.

(2) The antibody according to (1) above, wherein the mutant α-actinin-4 is a splice variant derived from exon 8' of DNA encoding α-actinin-4.

(3) The antibody according to (1) above, wherein the substituted amino acid residue(s) is at least one selected from the group consisting of glycine at position 248, leucine at position 250 and cysteine at position 263 in the amino acid sequence of α-actinin-4.

(4) The antibody according to (1) above, wherein the amino acid sequence with substituted amino acid residue(s) is represented by DIVGTLRPDEKAIMTYVSC (SEQ ID NO: 4).

(5) The antibody according to (1) above, wherein the antibody is a monoclonal antibody.
(6) The antibody according to (5) above, which is produced by a hybridoma having Accession No. NITE BP-1140.
(7) An antibody binding to an epitope, to which the antibody according to (5) or (6) above binds.
(8) The antibody according to (5) or (6) above, wherein the antibody is a chimeric antibody, a humanized antibody or a reconstituted human antibody.
(9) A fragment of the antibody according to any one of (1) to (8) above.
(10) A hybridoma producing the antibody according to (5) or (6) above.
(11) A hybridoma having Accession No. NITE BP-1140.
(12) A method for preparing an antibody against mutant α-actinin-4, which comprises the steps of:
  (a) immunizing a non-human mammal with a partial peptide comprising the amino acid sequence of the region between position 245 to 263 of α-actinin-4, wherein the partial peptide has at least one amino acid residue substitution in said region; and
  (b) collecting the antibody from the non-human mammal.
(13) A method for preparing a monoclonal antibody against mutant α-actinin-4, which comprises the steps of:
  (a) immunizing a non-human mammal with a partial peptide comprising the amino acid sequence of the region between 245 to 263 of α-actinin-4, wherein the partial peptide has at least one amino acid residue substitution in said region;
  (b) collecting antibody-producing cells from the immunized non-human mammal above;
  (c) allowing the antibody-producing cells obtained in step (b) to be fused with myeloma cells; and
  (d) collecting the antibody from the fusion cells obtained in step (c).
(14) The method according to (12) or (13) above, wherein the non-human mammal is a GANP transgenic non-human mammal.
(15) A method for detecting mutant α-actinin-4, which is characterized by reacting the antibody according to any one of (1) to (9) above or a fragment thereof with a biological sample to thereby detect mutant α-actinin-4.
(16) A method for detecting a gene encoding mutant α-actinin-4 comprising an amino acid sequence with at least one amino acid residue substitution in the region between position 245 and 263 of α-actinin-4, wherein said method comprises reacting a biological sample with a probe for a polynucleotide encoding the substituted amino acid sequence or primers for amplification of said polynucleotide to thereby detect the gene.
(17) The method according to (16) above, wherein the gene encoding mutant α-actinin-4 is mRNA of a splice variant derived from exon 8' of DNA encoding a-actinin-4.
(18) A method for detecting a tumor by using the detection results obtained by the method according to any one of (15) to (17) above.
(19) A method for evaluating the state of a tumor or the state of prognosis by using the detection results from the method according to any one of (15) to (18) above as an indicator..
(20) A reagent for tumor detection or diagnosis, which comprises the antibody according to any one of (1) to (9) above or a fragment thereof.
(21) A reagent for tumor detection or diagnosis, which comprises a probe for a polynucleotide encoding an amino acid sequence with at least one amino acid residue substitution in the region between position 245 and 263 of α-actinin-4 or primers for amplification of said polynucleotide.
(22) The method according to (18) or (19) above, wherein the tumor is lung primary high-grade neuroendocrine tumor.
(23) The reagent according to (20) or (21) above, wherein the tumor is lung primary high-grade neuroendocrine tumor.
(24) An antitumor pharmaceutical composition, which comprises a substance inhibiting the functions of mutant α-actinin-4 comprising an amino acid sequence with at least one amino acid residue substitution in the region between position 245 and 263 of α-actinin-4.
(25) The pharmaceutical composition according to (24) above, wherein the substance inhibiting the functions of mutant α-actinin-4 is the antibody according to any one of (1) to (9) above or a fragment thereof, or an inhibitory nucleic acid against a gene encoding mutant α-actinin-4.
(26) The pharmaceutical composition according to (24) or (25) above, wherein the tumor is lung primary high-grade neuroendocrine tumor.

Advantageous Effects of Invention

The present invention provides an antibody against mutant ACTN4, more specifically a specific antibody against ACTN4-Va, as well as a cell line producing such an antibody. Moreover, the present invention provides a method for detecting ACTN4-Va, which is characterized by reacting the above antibody with a biological sample, as well as a reagent for detecting ACTN4-Va.

The monoclonal antibody of the present invention which reacts with ACTN4-Va allows highly sensitive and specific detection of ACTN4-Va in specimens such as tissues, cells and blood; and hence it is useful for diagnosis of tumors, preferably cancers.

BRIEF DESCRIPTION OF THE DRAWINGS

The patent or application file contains at least one color drawing. Copies of this patent or patent application publication with color drawings will be provided by the USPTO upon request and payment of the necessary fee.

It should be noted that the respective symbols in the figure are as follows.
  (1 in a circle): MCF7-derived extract
  (2 in a circle): 1169-derived extract
  (3 in a circle): BxPC-3-derived extract
  I: ACTN4-Va antibody (11H2)
  II: ACTN4-Va antibody (15H2)
  III: ACTN4-Va antibody (10E10)
  IV: ACTN4-Va antibody (13G9)
  V: ACTN4-Va antibody (9B3)
  M: Size marker
  P: Positive control ACTN4-N antibody (13G9)

Figure 4:
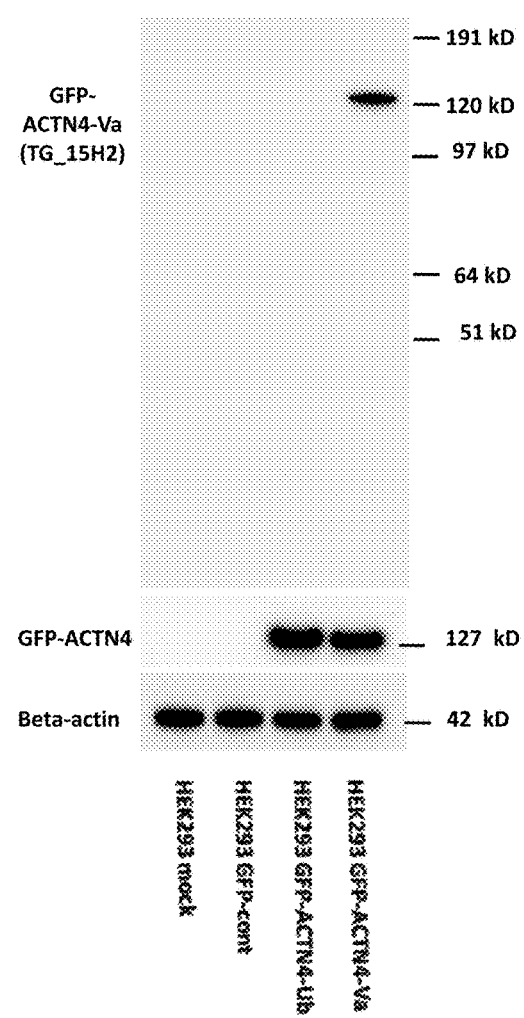

FIG. 4 shows the results of verification testing for specificity in ACTN4-Va gene-introduced cells, as determined by Western blotting with a monoclonal antibody derived from clone "15H2."

Figure 5:
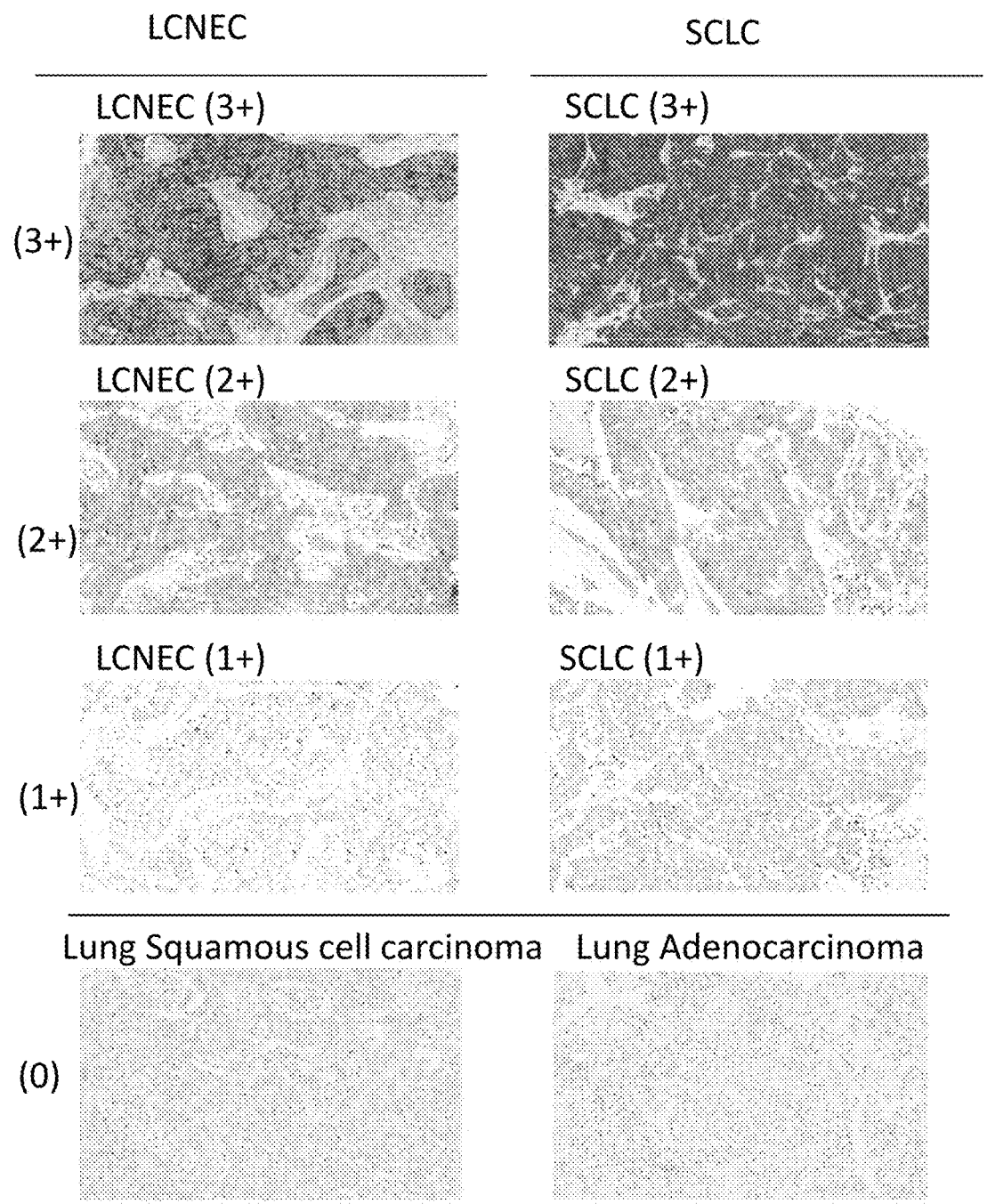

FIG. 5 shows the results of diagnosis compatibility testing in HGNT, as determined by immunohistochemical staining against ACTN4-Va with a monoclonal antibody derived from clone "15H2."

Figure 6:
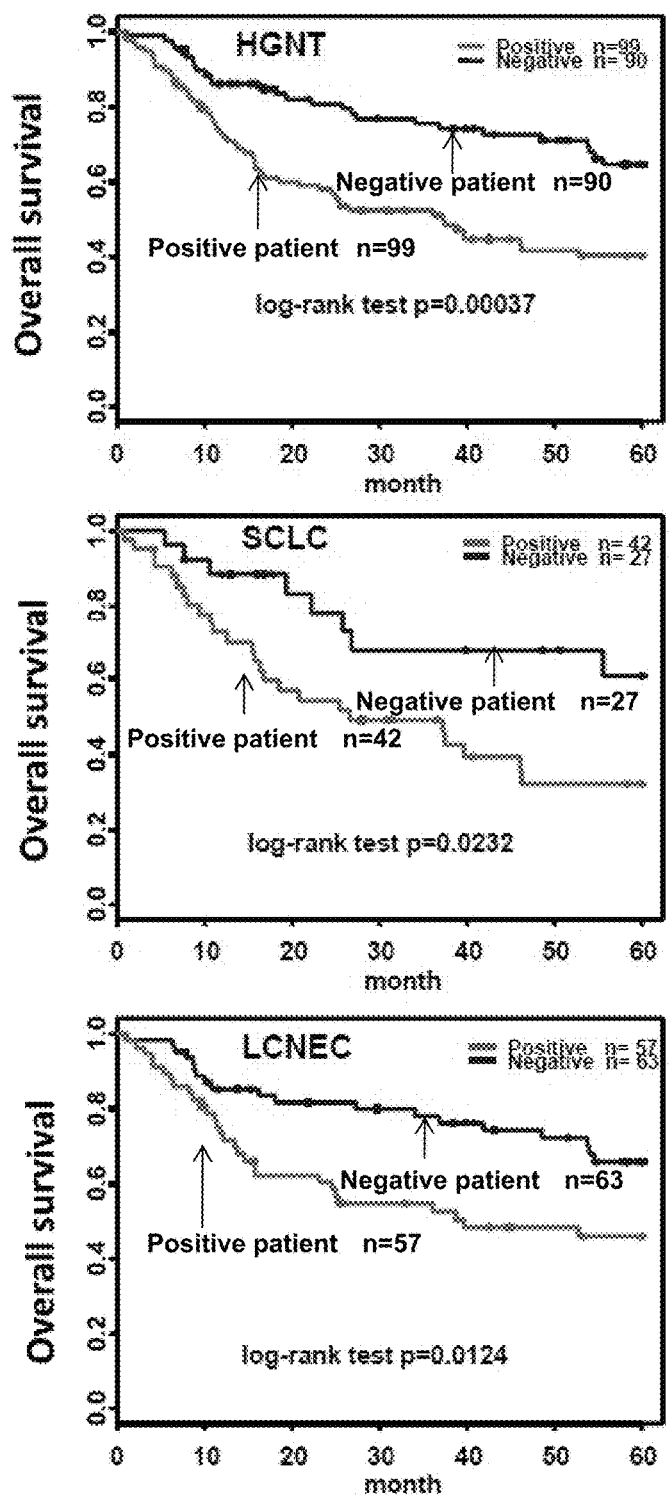

FIG. 6 shows the results analyzed for ACTN4-Va protein expression and prognosis in HGNT, SCLC and LCNEC patients.

Figure 7:
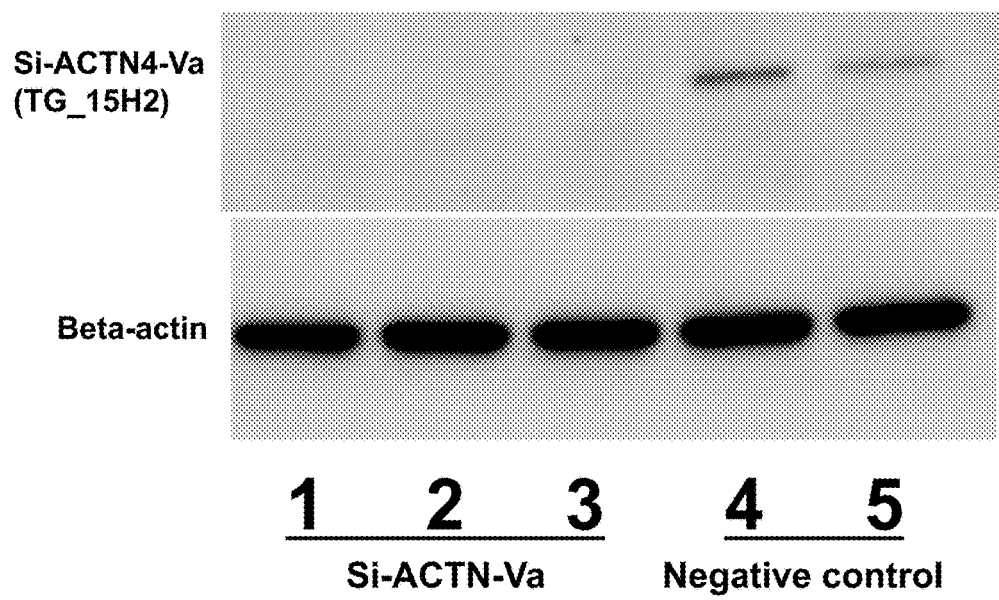

FIG. 7 shows the results indicating siRNA-mediated suppression of ACTN4-Va expression.

BEST MODES FOR CARRYING OUT THE INVENTION

The present invention is directed to an antibody against mutant α-actinin-4 having an amino acid sequence with at least one amino acid residue substitution in the region between position 245 and 263 of α-actinin-4, and the antibody of the present invention recognizes all or a part of the amino acid residue(s) substituted in the above region between position 245 and 263 (i.e., the substituted amino acid residue(s)). In one embodiment of the present invention, mutant α-actinin-4 recognized by the antibody of the present invention is a splice variant derived from exon 8' of DNA encoding α-actinin-4.

The present invention is further directed to an antibody which distinguishes and binds to ACTN4-Va because of reacting with ACTN4-Va but not with ACTN4-Ub.

1. The Antibody of the Present Invention

The antibody of the present invention is an antibody against mutant ACTN4 (protein or polypeptide) comprising an amino acid sequence with amino acid substitution in an ACTN4 molecule.

As used herein, the terms "α-actinin-4," "ACTN4," "mutant actinin-4," "ACTN4-Va," "splice variant," "ACTN4-Ub" and others are intended to encompass full-length proteins, partial polypeptides and partial peptides, unless otherwise specified. Thus, for example, the expression "the antibody of the present invention recognizes ACTN4-Va" should be interpreted to mean that the antibody of the present invention recognizes both the full-length protein of ACTN4-Va (e.g., a splice variant of ACTN4), and a partial polypeptide of ACTN4-Va (e.g., a partial polypeptide comprising a region with amino acid substitution(s) in a splice variant derived from exon 8' in ACTN4).

In a preferred embodiment of the present invention, the antibody of the present invention has at least one property selected from (i) to (iii) shown below.
(i) An antibody against ACTN4-Va that satisfies the requirement to recognize all or any of newly inserted exon 8'-derived amino acid sequence substitutions.
(ii) The above amino acid substitutions are glycine (G) at position 248, leucine (L) at position 250 and cysteine (C) at position 263 of the amino acid sequence.
(iii) The amino acid sequence of its antigen is represented by DIVGTLRPDEKAIMTYVSC (SEQ ID NO: 1).

Amino acid residue substitution sites and the substituted amino acid residues are at least one amino acid residue in an amino acid sequence between aspartic acid at position 245 and serine at position 263. Preferably, glycine at position 248, leucine at position 250, cysteine at position 263 is substituted, and these amino acid residue substitutions are either alone or in combination.

The amino acid sequence of ACTN4 is shown in SEQ ID NO: 2. In SEQ ID NO: 2, an amino acid sequence derived from exon 8 is an amino acid sequence between aspartic acid at position 245 and serine at position 263 (DIVNTARPDEKAIMTYVSS (SEQ ID NO: 3)).

Thus, in the present invention, mutant ACTN4 is designed that at least one amino acid residue in the amino acid sequence between aspartic acid at position 245 and serine at position 263 is substituted with other amino acid residue(s). Preferably, mutant ACTN4 is designed that valine at position 248 in the amino acid sequence of wild-type ACTN4 mutates into glycine, alanine at position 250 mutates into leucine, and serine at position 263 mutates into cysteine, or any one or two of these mutations. Such mutation includes mutations caused by the insertion of exon 8' in place of exon 8, i.e., a splice variant (Non-patent Document 5). An amino acid substitution resulting in such a mutation is also herein referred to as an "ACTN4-Va-specific amino acid sequence substitution."

Thus, in a more preferred embodiment of the present invention, the antibody of the present invention is a high-specificity antibody which binds specifically to a partial fragment comprising an amino acid sequence in which amino acid residue in newly inserted exon 8'-derived novel splice variant is substituted in the amino acid sequence of ACTN4-Va or to the full length thereof. The antibody against mutant ACTN4 (including an antibody against a splice variant) is also hereinafter referred to as an "anti-ACTN4-Va antibody."

In the context of the present invention, the expression "bind specifically" or "recognize" is intended to mean binding to (reacting with) mutant ACTN4 (ACTN4-Va), e.g., all or one (at least one) of the substituted amino acid residues, but not binding to (reacting with) ACTN4-Ub bearing no mutation. The region to which the antibody of the present invention binds or recognizes is not limited only to the substituted amino acid residues, but includes any other regions as long as they comprise the substituted amino acid residues. Namely, the region to which the antibody of the present invention binds or recognizes does not exclude any region of the unsubstituted amino acid sequence.

Determination of whether the binding is specific or not may be accomplished by immunological procedures, such as ELISA, Western blotting, or immunohistochemical staining, etc.

2. Preparation of Antibody

The preparatopm method of the antibody of the present invention will then be described below.

2-1. Preparation of Antigen

ACTN4-Va is expressed only in small cell lung cancer patient tissues, small cell lung cancer-derived cell lines, or testis among normal tissues. Moreover, the desired antigen site is any of the above three amino acids derived from amino acid sequence substitutions present in a novel splice variant. For this reason, in the case of preparing an immunizing antigen for desired antibody, a tissue- or cell-derived antigenic protein comprising the full-length sequence is not appropriate. It is therefore necessary to synthesize an immunizing antigen comprising a sequence with amino acid substitution(s).

In the present invention, a partial peptide of ACTN4-Va is synthesized and used as an immunizing antigen. However, a synthetic peptide is a small molecule and it is difficult to obtain an antibody when a mouse is immunized with such a small molecule directly. For this reason, a synthetic peptide and a carrier protein are linked via disulfide binding by MBS method to prepare an immunizing antigen.

In the present invention, an immunizing antigen can be prepared according to a known manner (Fmoc method, Kunio Fujiwara. et al., Journal of Immunological Methods, 61, 217-226 (1983)).

Chemical synthesis of peptides may be accomplished by techniques known to those skilled in the art, such as Fmoc method (fluorenylmethyloxycarbonyl method), tBoc method (t-butyloxycarbonyl method), etc.

Carrier proteins which can be used for this purpose may include BSA (bovine serum albumin), as well as KLH (keyhole limpet hemocyanin), OVA (ovalbumin) and so on. Those skilled in the art would be able to prepare an immunizing antigen by a known method.

An amino acid sequence based on which an antigen peptide is synthesized is a partial sequence in ACTN4-Va, from which any amino acid sequence of 10 to 50 contiguous residues, preferably 10 to 30 contiguous residues, more preferably 15 to 20 contiguous residues in length may be selected. As to the criteria for selection, it is necessary to comprise at least one ACTN4-Va-specific amino acid sequence substitution in the selected amino acid sequence. These amino acid residues are used for peptide synthesis.

A peptide which can be used as an antigen is preferably a peptide of the region between 245 and 263 in the amino acid sequence shown in SEQ ID NO: 2, and a peptide comprising at least one amino acid substitution in the above region as a peptide containing ACTN4-Va-specific amino acid sequence substitution(s). Preferably, a peptide with at least one substitution of valine at position 248, alanine at position 250, and serine at position 263 in the above region is used. It is more preferred to use a partial peptide of ACTN4-Va (e.g., DIVGTLRPDEKAIMTYVSC (SEQ ID NO: 4)) which comprises amino acid residues where substitution mutations have occurred upon exon 8' insertion, i.e., asparagine at position 248 in the amino acid sequence shown in SEQ ID NO: 2 has been mutated to glycine (N248G), alanine at position 250 has been mutated to leucine (A250L) and serine at position 263 has been mutated to cysteine (S263C).

It should be noted that ACTN4-Va-specific amino acid sequence substitutions are not limited only to the above N248G, A250L and S263C, and the substituted amino acid residues may be any of the other 18 types of amino acid residues except for N and G (i.e., A, R, D, C, Q, E, H, I, L, K, M, F, P, 5, T, W, Y or V) at position 248, any of the other 18 types of amino acid residues except for A and L (i.e., R, N, D, C, Q, E, G, H, I, K, M, F, P, S, T, W, Y or V) at position 250, and any of the other 18 types of amino acid residues except for S and C (i.e., A, R, N, D, Q, E, G, H, I, L, K, M, F, P, T, W, Y or V) at position 263.

2-2. Preparation of Polyclonal Antibody

The partial peptide prepared as above is administered directly or together with a carrier or a diluent to immunize non-human mammals, followed by measurement of their antibody titers.

Non-human mammals to be immunized may not be limited, and examples include mice, rats, guinea pigs, rabbits, dogs, goats and so on, with mice being preferred.

In a preferred embodiment of the present invention, as an animal to be immunized for preparation of the antibody of the present invention, a transgenic non-human mammal called "GANP (registered trademark)" which has the ability to produce high-specificity antibody (WO2004/040971) can be used.

This GANP transgenic non-human mammal refers to a non-human mammal in which a gene encoding a germinal center-associated nuclear protein is introduced, and when immunized with a given antigen, the animal will be able to produce an antibody with high-affinity or high-specificity against the antigen (WO00/50611, Sakaguchi N. et al., J Immunol. 2005 Apr. 15; 174(8):4485-94).

For example, GANP transgenic non-human mammals (e.g., mice) may be prepared as described in the above patent publication or the above document of Sakaguchi et al., or alternatively, may be obtained as commercially available GANP mice (Trans Genic Inc., Ltd., Japan).

The dosage amount of an antigen per animal is 10 to 2000 μg in total. For antigen immunization, it is common to mix an adjuvant with an antigen solution, and the type of adjuvant includes Freund's complete adjuvant (FCA), Freund's incomplete adjuvant (FIA), aluminum hydroxide adjuvant and others. Immunization is accomplished primarily by injection via the intravenous, subcutaneous, intraperitoneal, intramuscular or footpad subcutaneous route, etc. The interval of immunization is not limited in any way, and immunization may be repeated once to 10 times, preferably twice to 5 times, at intervals of several days to several weeks, preferably at intervals of 2 to 3 weeks.

Once antibody titers have been elevated to an absorbance level of 2 or higher upon immunization, the animals are allowed to stand for 2 to 6 months, preferably for 4 to 6 months, more preferably for 6 months, until the antibody titers are reduced to an absorbance level of 0.05 to 1, preferably 0.05 to 0.5, more preferably 0.05. It should be noted that the serum dilution ratio showing the above absorbance level is 27.000-fold, by way of example.

For immunization in GANP transgenic non-human mammals, there is no need to allow the animals to stand until the absorbance level is reduced, so that immunization may be repeated according to the immunization intervals of common monoclonal antibody preparation procedures until the final immunization.

Antibody titers can be examined by using blood samples collected from the immunized animals. The collected blood samples are each preferably immediately centrifuged to separate serum without being stored at low temperature after blood collection. The sera obtained may be serially diluted and measured for antibody titers by ELISA (enzyme-linked immunosorbent assay) or EIA (enzyme immunoassay), RIA (radioimmuno assay), etc. In cases where antibody titers are measured by ELISA or EIA, the absorbance may be measured with a spectrophotometer.

As a result of measurement, the animals showing high antibody titers against ACTN4-Va are subjected to the final immunization. However, antigen immunization and antibody titer measurement are not limited to the above procedures.

Subsequently, immunocompetent cells (e.g., spleen cells) are excised after several days, preferably after 3 to 5 days, from the final immunization date. In cases where the antigen is injected into the animals via the footpad subcutaneous route, the final immunization is conducted once, and immunocompetent cells (e.g., spleen cells) or regional lymph nodes are excised after 7 to 13 days, preferably after 8 to 10 days, from the final immunization. As to the interval of blood collection, blood is collected after 1 to 4 weeks, preferably after 1 to 2 weeks, from the immunization.

In the present invention, for obtaining polyclonal antibodies, blood is collected at the date when the animals showed the above desired antibody titer, and treated to obtain antiserum. If antibodies are required to be purified, known purification method such as ammonium sulfate precipitation, ion exchange chromatography, gel filtration chromatography, affinity chromatography and so on may be selected as appropriate or used in combination for this purpose. Subsequently, polyclonal antibodies in the antiserum are measured for their reactivity by ELISA or other assays.

2-3. Preparation of Monoclonal Antibody Against ACTN4-Va

The preparation method of a monoclonal antibody against ACTN4-Va will be described below, but is not limited to the following.

To obtain the monoclonal antibody of the present invention ("anti-ACTN4-Va antibody"), a peptide of a novel splice variant comprising substituted amino acid residues is first immunized into animals such as GANP transgenic non-human mammals, and antibody-producing cells (e.g., B cells) are collected from the immunized animals and fused with myeloma cells to prepare hybridomas (fused cell lines). Then, antibodies produced from these hybridomas are collected, whereby the desired monoclonal antibody can be obtained.

The anti-ACTN4-Va antibody is a so-called hapten antibody. For preparation of such a hapten antibody, the molecular structure design of a hapten-carrier conjugate will greatly affect the performance of a specific antibody.

(1) Preparation of Antibody-Producing Cells

Antibody-producing cells are prepared from, e.g., spleen cells or regional lymph nodes of the immunized animals (e.g., non-human mammals). When using GANP transgenic non-human mammals, antibody-producing cells can also be collected from their spleen cells or lymph nodes, as in the case above. Examples of lymph nodes include inguinal lymph nodes, mediastinal lymph nodes and so on. Although there is no particular need to separate antibody-producing cells from the collected cell populations, it is preferred to separate only antibody-producing cells from among the cell populations. Moreover, for preparation of antibody-producing cells, it is preferred to remove tissue debris and erythrocytes as much as possible. For removal of erythrocytes, it is preferred to use commercially-available erythrocyte removal solution or to use a neutral buffer which is prepared from ammonium chloride and tris. If the prepared antibody-producing cells are not provided for the following manipulation immediately after their preparation, the state of the cells may be deteriorated, so that the prepared cells are preferably allowed to stand on ice if it takes time before the subsequent manipulation.

(2) Cell Fusion

Cell fusion is a manipulation to fuse the above antibody-producing cells with myeloma cells for the preparation of cells that semipermanently continue to grow while producing antibodies (hybridomas). As myeloma cells to be fused with antibody-producing cells, commonly available cell line of animal (e.g., mouse) origin can be used. Cell lines preferred for use are those having the property of not surviving in HAT selective medium (i.e., a medium containing hypoxanthine, thymidine and aminopterin), but surviving only when fused with antibody-producing cells. Examples of myeloma cells include P3X63-Ag.8.U1 (P3U1), P3/NS I/1-Ag4-1(NS I) and so on.

Cell fusion may be accomplished as follows: spleen cells and/or lymph node cells at $1\times10^6$ to $1\times10^7$ cells/mL are mixed with myeloma cells at $1\times10^5$ to $1\times10^6$ cells/mL (the ratio of spleen cells and/or lymph node cells to myeloma cells is preferably 5:1) in a commercially available medium (e.g., DMEM or RPMI 1640 medium) without fetal bovine serum (FCS) and others to cause cell fusion in the presence of a cell fusion promoter. As a cell fusion promoter, polyethylene glycol having an average molecular weight of 200 to 20000 daltons can be used.

Alternatively, a commercially available cell fusion apparatus using electrical stimulation (e.g., electroporation) may also be used to cause cell fusion. Further, Sendai virus may also be used to cause cell fusion. Those skilled in the art would be able to fuse the above antibody-producing cells with myeloma cells by using known cell fusion techniques.

After cell fusion, the cells are diluted with HAT medium prepared from, e.g., 10% to 20% (preferably 20%) FCS-containing RPMI 1640 medium or the like, and then seeded into each well of a 96-well culture plate at 0.5 to $3\times10^5$ cells per well and cultured in a $CO_2$ incubator.

(3) Establishment of Hybridoma

Subsequently, the cells obtained by cell fusion are screened to select a hybridoma producing a desired antibody. After 10 to 14 days from the cell fusion, the cells selected as above with HAT medium will form colonies. The culture supernatants of colony-positive wells in the 96-well culture plate are collected and confirmed for their antibody titer against ACTN4-Va. Confirmation may be accomplished by enzyme immunoassay techniques (ELISA) or radioactive immunoassay techniques (RIA), etc. At this stage, antibodies produced from the cells include antibodies against KLH or BSA used as a carrier protein. By measuring antibody titers against KLH and others, it is possible to eliminate KLH antibody-positive wells showing high antibody titers against KLH and others. Upon confirmation of wells positive to antibody production against ACTN4-Va, cells in these wells are transferred to a 24-well or 12-well culture plate.

At this stage, the medium is preferably replaced with aminopterin-free HT medium (i.e., a medium containing hypoxanthine and thymidine). HT medium is used as a hybridoma recovery medium which continues to supply purine and pyrimidine precursors to the salvage pathway for a period under the effect of residual aminopterin in the cells. After the cultivation in HT medium for a while, antibody titers in the culture supernatants are confirmed again. Hybridomas are unstable because of being fused cells, and hence are likely to lose their antibody production ability quickly. For this reason, it is preferred to perform the second confirmation of antibody titers. As described above, in the present invention, it is necessary to obtain a hybridoma which does not cross-react with ACTN4-Ub and has high specificity for ACTN4-Va. It is therefore important here to confirm other cross-reactivity with ACTN4-Ub at the culture supernatant level by ELISA or RIA, etc.

Cells in the finally selected wells are cloned into single cells. Cloning may be accomplished as follows: cell suspensions are each diluted as appropriate with, e.g., 10% to 20% (preferably 20%) FCS-containing RPMI 1640 medium or the like, and then seeded into each well of a 96-well culture plate at a density of 0.3 to 2 cells per well. As for the number of cells in each well of the 96-well culture plate, to ensure a high probability that one well contains one cell, the cells are preferably seeded such that each well contains one cell. 7 to 10 days after seeding the cells, the culture supernatants of colony-positive wells are collected. In this case, confirmation of whether a single colony is formed is preferably performed 3 to 5 days later. The collected culture supernatants are confirmed for their antibody titers. Also in this case, a clone which has high specificity for ACTN4-Va and low cross-reactivity with ACTN4-Ub should be selected. Further, cells in the selected well are allowed to grow to some extent to thereby establish a hybridoma line. Cloning may be repeated several times as needed.

(4) Preparation of Monoclonal Antibody

ACTN4-Va-specific monoclonal antibody is purified and collected from the established hybridoma line in the following manner. Namely, the antibody may be prepared from the culture supernatant cultured in a medium with reduced serum concentration or from the culture supernatant cultured in a commercially available serum-free medium, or alternatively, the hybridoma may be injected intraperitoneally to an animal to collect the peritoneal fluid, from which the antibody is then prepared. The culture supernatant is collected from cells which have been prepared at 0.1 to $4 \times 10^5$ cells/mL and cultured for 1 to 2 weeks. As of the peritoneal fluid, 0.1 to $1 \times 10^7$ cells of hybridoma is intraperitoneally administered to an animal of the same species as the mammal from which myeloma cells are derived, whereby the hybridoma is allowed to grow in abundance. Then, after 1 to 2 weeks, the peritoneal fluid is collected.

Cultivation methods include those using a culture flask, a spinner flask, a shaker flask, a bioreactor, and the like. Antibody purification methods include purification with a Protein G affinity column or with a Protein A affinity column, purification with an ACTN4-Va affinity column, purification by ammonium sulfate precipitation and the subsequent gel filtration chromatography, purification by ion exchange chromatography, etc., and these known techniques may be selected as appropriate or used in combination for purification purposes. It should be noted that when a Protein A affinity column is used for mouse $IgG_1$ purification, it is effective to use a buffer optimized for binding conditions, and those skilled in the art would be able to select optimum conditions as appropriate for purification.

(5) Deposition of microorganism

The cell line (hybridoma) producing the monoclonal antibody of the present invention is designated as "Anti ACTN4-Va MAb (Clone No. 15H2)" and was internationally deposited on Aug. 31, 2011 with the National Institute of Technology and Evaluation, Patent Microorganisms Depositary (Patent Microorganisms Depositary, Department of Biotechnology of NITE, 2-5-8 Kazusakamatari, Kisarazu-shi, Chiba 292-0818, Japan). Its accession number (indicated in the receipt), which represents the receipt number, is NITE BP-1140. NITE BP-1140 is a clone established as "15H2" in Example 1.

(6) Characteristics of Monoclonal Antibody

The monoclonal antibody of the present invention binds specifically to and shows high specificity for ACTN4-Va. The specificity satisfies the conditions where specificity can be indicated by Western blotting in the reaction system between ACTN4-Va and antibody if a band of ACTN4-Va is detected at the position of the desired molecular weight in the antigen-antibody reaction system using a cell extract of human small cell lung cancer-derived cancer cell line H69 where ACTN4-Va is specifically expressed, in comparison with the antigen-antibody reaction systems using cell extracts of non-expressing lines, i.e., human pancreatic adenocarcinoma-derived cell line BxPC-3 and human breast cancer-derived cell line MCF7.

For example, (i) First, an extract of human small cell lung cancer-derived cancer cell line H69 comprising ACTN4-Va with newly inserted exon 8'-derived amino acid sequence substitutions (this extract is referred to as "antigen 1") is provided for Western blotting. Likewise, cell extracts of human pancreatic adenocarcinoma-derived cell line BxPC-3 and human breast cancer-derived cell line MCF7, each comprising ACTN4-Ub without newly inserted exon 8'-derived amino acid sequence substitutions (these extracts are referred to as "antigen 2" and "antigen 3," respectively) are also provided for Western blotting.

(ii) Next, antibodies against these antigens are allowed to react with their respective antigens at the same concentration.

The antigen molecule (antigen 1) in the above antigen-antibody reaction (i) has newly inserted exon 8'-derived amino acid sequence substitutions in its amino acid sequence, so that the monoclonal antibody of the present invention binds specifically to immobilized antigen 1 which comprises newly inserted exon 8'-derived amino acid sequence substitutions. As a result, the antigen 1 can be detected by Western blotting as a protein band with a molecular weight of approximately 100 KDa.

On the other hand, in cases where the immobilized antigen in the above reaction system is antigen 2 or antigen 3, newly inserted exon 8'-derived amino acid sequence substitutions don't exist in these antigens, so that immobilized antigens 2 and 3 cannot not bind specifically to the monoclonal antibody of the present invention. As a result, no reaction product can be detected by Western blotting as a protein band with a molecular weight of approximately 100 KDa.

When tested by the above antigen-antibody reaction on the condition that antigens 1, 2 and 3 are electrophoresed in an amount of 10 µg/lane, the antibody of the present invention satisfies the detection condition that detectable concentration of anti-ACTN4-Va is at least 10 µg/ml or less, preferably 5 µg/ml or less, more preferably 2.5 µg/ml or less, particularly preferably 1 µg/ml or less. Thus, the antibody of the present invention has very high specificity for antigen 1.

Alternatively, Western blotting using an antigen derived from ACTN4-Va-transformed expressing cells may be performed to indicate the specificity of this monoclonal antibody.

The specificity can be detected as follows.

For Western blotting in the reaction system between ACTN4-Va and antibody, a plasmid vector carrying GFP (green fluorescent protein) added at the N-terminal end of ACTN4-Va is prepared and transformed into human renal epithelial cell line HEK293 (hereinafter referred to as HEK293), and an extract derived from the thus transformed expressing cells is provided for the antigen-antibody reaction system (hereinafter referred to as reaction system 1). On the other hand, a plasmid vector carrying GFP (green fluorescent protein) added at the N-terminal end of ACTN4-Ub is prepared and transformed into HEK293, and an extract derived from the thus transformed expressing cells is provided for the antigen-antibody reaction system (hereinafter referred to as reaction system 2).

Next, reaction system 1 and reaction system 2 are compared with each other to detect whether a band of ACTN4-Va appears at the position of the desired molecular weight in reaction system 1.

(7) Antibody Fragments

Fragments of the above antibody also fall within the antibody of the present invention. In the context of the present invention, the antibody fragments of the present invention are those against ACTN4-Va which have the above ability that recognize all or any of newly inserted exon 8'-derived amino acid sequence substitutions, as in the case of the antibody of the present invention.

A fragment of the antibody is intended to mean a partial region of the antibody of the present invention, and examples include Fab (antigen-binding fragment), Fab', $F(ab')_2$, Fv, diabody (dibodies), dsFv, linear antibody, scFv (single chain Fv), peptides containing complementarity determining regions (CDRs) as at least a part thereof, and so on. The above antibody fragments may be obtained by cleaving the antibody of the present invention with various proteases depending on the intended purpose.

For example, Fab may be obtained by treating an antibody molecule with papain, while F(ab')$_2$ may be obtained by treating an antibody molecule with pepsin. Likewise, Fab' may be obtained by cleaving the disulfide bonds in the hinge region of the above F(ab')$_2$.

In the case of scFv, cDNAs encoding antibody VH and VL may be obtained to construct DNA encoding scFv. This DNA may be inserted into an expression vector, and scFv may be produced by introducing the resulting expression vector into a host organism and expressing in said host organism.

In the case of diabody, cDNAs encoding antibody VH and VL may be obtained to construct DNA encoding scFv such that the amino acid sequence of a peptide linker has a length of 8 residues or less. This DNA may be inserted into an expression vector, and diabody may be produced by introducing the resulting expression vector into a host organism and expressing in said host organism.

In the case of dsFv, cDNAs encoding antibody VH and VL may be obtained to construct DNA encoding dsFv. This DNA may be inserted into an expression vector, and dsFv may be produced by introducing the resulting expression vector into a host organism and expressing in said host organism.

In the case of a CDR-containing peptide, DNA encoding CDRs in antibody VII and VL may be constructed. This DNA may be inserted into an expression vector, and a CDR-containing peptide may be produced by introducing the resulting expression vector into a host organism and expressing in said host organism. Alternatively, a CDR-containing peptide may also be prepared by chemical synthesis such as Fmoc method and tBoc method.

Even if the amino acid sequence of the antibody is modified, such an antibody falls within the scope of the present invention as long as it is able to bind specifically to the above mutant ACTN4.

(8) Gene Recombinant Antibody

A preferred embodiment of the antibody against ACTN4-Va according to the present invention may be a gene recombinant antibody. Examples of a gene recombinant antibody include, but are not limited to, a chimeric antibody, a humanized antibody and a reconstituted human antibody, etc.

A chimeric antibody (i.e., a humanized chimeric antibody) is an antibody in which antibody variable regions of mouse origin are linked (conjugated) to constant regions of human origin (see, e.g., Proc. Natl. Acad. Sci. U.S.A. 81, 6851-6855, (1984)). For preparation of a chimeric antibody, gene recombination technology may be used for its construction to obtain thus linked antibody.

For preparation of a humanized antibody, a method called CDR grafting (CDR transplantation) can be used. CDR grafting is a technique to prepare reconstituted variable regions whose framework regions (FRs) are of human origin and whose CDRs are of mouse origin by transplanting complementarity determining regions (CDRs) from mouse antibody variable regions to human variable regions. Next, these humanized reconstituted human variable regions are linked to human constant regions. Procedures for preparation of such a humanized antibody are well known in the art (see, e.g., Nature, 321, 522-525 (1986); J. Mol. Biol., 196, 901-917 (1987)).

A reconstituted human antibody (complete human antibody) is an antibody in which hyper variable regions serving as general antigen-binding sites in the V regions, other regions in the V regions, and the constant regions have the same structures as those of human antibody. However, hyper variable regions may be of other animal origin. Techniques for reconstituted human antibody preparation are also known, and a method to prepare a gene sequence common to human has been established by genetic engineering procedures. Such a reconstituted human antibody may be obtained, for example, by using human antibody-producing mice which have human chromosome fragments comprising genes for human antibody H and L chains (see, e.g., Tomizuka, K. et al., Nature Genetics, (1977) 16, 133-143; Kuroiwa, Y. et al., Nuc. Acids Res., (1998) 26, 3447-3448; Yoshida, H. et al., Animal Cell Technology: Basic and Applied Aspects, (1999) 10, 69-73 (Kitagawa, Y., Matuda, T. and Iijima, S. eds.), Kluwer Academic Publishers; Tomizuka, K. et. al., Proc. Natl. Acad. Sci. USA, (2000) 97, 722-727) or by obtaining a phage display-derived human antibody selected from human antibody libraries (see, e.g., Wormstone, I. M. et al, Investigative Ophthalmology & Visual Science., (2002) 43 (7), 2301-8; Carmen, S. et al., Briefings in Functional Genomics and Proteomics, (2002) 1 (2), 189-203; Siriwardena, D. et al., Opthalmology, (2002) 109 (3), 427-431).

Alternatively, in the present invention, the hybridoma of the present invention (e.g., the hybridoma under Accession No. NITE BP-1140) or DNA or RNA extracted from this hybridoma may be used as a starting material to prepare a chimeric antibody, a humanized antibody or a reconstituted human antibody in accordance with the well-known methods mentioned above.

(9) Antibody Binding to an Antigenic Determinant, to which the Antibody of the Present invention binds Further, the anti-ACTN4-Va antibody of the present invention may preferably be exemplified by, e.g., an antibody binding to a site (e.g., an epitope) to which a monoclonal antibody produced by the hybridoma under Accession No. NITE BP-1140 binds (recognizes). Examples of such an epitope include those illustrated below.

The epitope (antigenic determinant) for the anti-ACTN4-Va antibody of the present invention is not limited in any way as long as it is at least a part of the antigen ACTN4-Va, and examples include a region comprising the amino acid sequence located at positions 245 to 263 in the amino acid sequence of ACTN4, wherein the residues at positions 248, 250 and 263 are replaced with other amino acid residues, preferably glycine, leucine and cysteine, respectively. The amino acid sequence of such an epitope is represented by DIVGTLRPDEKAIMTYVSC (SEQ ID NO: 4).

3. Detection Method

ACTN4-Va can be used as a clinical marker (tumor marker) for cancer. Thus, when the antibody of the present invention is reacted with a biological sample to measure ACTN4-Va in the biological sample, the measurement results can be used as an indicator for tumor detection or diagnosis.

Thus, the present invention provides a method for detecting mutant α-actinin-4, which comprises reacting the antibody of the present invention or a fragment thereof with a biological sample to thereby detect mutant α-actinin-4.

Moreover, the present invention also provides a method for cancer detection or diagnosis, which comprises reacting the antibody of the present invention with a biological sample to detect ACTN4-Va by means of the ability to react with ACTN4-Va but not with ACTN4-Ub. The protein to be detected may be exemplified by ACTN4-Va, and the target to be detected may be exemplified by the full-length protein of ACTN4-Va or a partial polypeptide of ACTN4-Va (e.g., a polypeptide comprising the following amino acid sequence).

(SEQ ID NO: 4)
DIVGTLRPDEKAIMTYVSC

ACTN4-Va may be measured by, but is not limited to, commonly used immunohistochemical staining (hereinafter referred to as IHC) or any technique known as hapten immunoassay (e.g., ELISA, EIA), etc.

Examples of cancer include, but are not limited to, at least one selected from the group consisting of brain tumor, salivary gland cancer, esophageal cancer, pharyngeal cancer, oral cancer, lung cancer, gastric cancer, small intestinal or duodenal cancer, colorectal cancer, urinary tract malignant tumors (e.g., prostate cancer, kidney cancer, bladder cancer, testis tumor), liver cancer, prostate cancer, breast cancer, uterine cancer, ovarian cancer, thyroid cancer, gallbladder cancer, biliary tract cancer, pancreatic cancer, neuroendocrine tumors, sarcomas (e.g., osteosarcoma, myosarcoma) and melanoma, although preferred is lung primary high-grade neuroendocrine tumor (HGNT). HGNT includes small cell lung cancer (SCLC) and large cell neuroendocrine carcinoma (LCNEC), and at least one selected from these may be exemplified. The type of cancer to be detected may be one or may be two or more occurring at the same time. The state of cancer is at least one selected from the group consisting of the presence or absence of cancer, the grade of malignancy of cancer, the presence or absence of cancer metastasis, and the presence or absence of cancer recurrence.

In particular, ACTN4-Va derived from HGNT patients comprises the amino acid sequence of the above peptide shown in SEQ ID NO: 4 (peptide with amino acid substitutions), and hence the antibody of the present invention which binds specifically to this amino acid sequence is particularly preferred for detection of the cancers mentioned above.

A biological sample is taken from a subject (e.g., a cancer patient, a patient suspected to have cancer, or a person undergoing medical examination) to prepare an ACTN4-Va test sample. Examples of such a biological sample include tissues, cells and so on. The taken tissue is preferably prepared into a tissue section for use as a sample.

Subsequently, the above test sample is reacted with the antibody of the present invention. Detection of ACTN4-Va may be accomplished by commonly used IHC. For convenience of explanation, mouse-derived antibody is used as an antibody of the present invention.

For measurement by IHC, paraffin on the section is removed and endogenous peroxidase activity is then blocked, followed by thermal treatment to cause antigen activation. Non-specific protein binding is blocked with 2% pig serum, followed by hybridization with a primary antibody (anti-ACTN4-Va antibody) at 4 C for 16 hours or longer. After washing out the primary antibody, biotinylated anti-mouse IgG is used as a secondary antibody to conduct hybridization at room temperature for 1 hour. After further washing, the section is reacted with an avidin peroxidase-labeled tertiary antibody, and DAB (3,3'-diaminobenzidine, tetrahydrochloride) is used as a substrate to develop color.

In another embodiment of the present invention, the amount of ACTN4-Va mRNA may be detected and the detection results may then be used for tumor detection.

Thus, the present invention provides a method for detecting a gene encoding mutant ACTN4 comprising an amino acid sequence with at least one amino acid substitution in the region between position 245 and 263 in the amino acid sequence of ACTN4. This method is designed to react a biological sample with a probe for a polynucleotide encoding the above substituted amino acid sequence or primers for amplification of the polynucleotide to thereby detect the above gene. The gene to be detected is preferably mRNA of a splice variant derived from exon 8' in DNA encoding ACTN4.

Measurement of mRNA may be carried out, for example, by Northern blotting, RT-PCR, real-time PCR, microarray analysis, etc.

The gene encoding ACTN4-Va has the substituted nucleotide sequence shown in SEQ ID NO: 1 which has substitution mutation(s) selected from the above N248G, A250L or S263C, or combinations thereof. Namely, V248G represents substitution of "ggc" (codon for Gly) for "aac" (codon for Asn) at positions 861 to 863 in the nucleotide sequence shown in SEQ ID NO: 1, A250L represents substitution of "cug" (codon for Leu) for "gcc" (codon for Ala) at positions 867 to 869 in the nucleotide sequence shown in SEQ ID NO: 1, and S263C represents substitution of "ugc" (codon for Cys) for "agc" (codon for Ser) at positions 906 to 908 in the nucleotide sequence shown in SEQ ID NO: 1.

Thus, in Northern blotting, a probe which hybridizes to nucleotides covering the above mutation site(s) (i.e., nucleotides derived from exon 8') in the gene encoding ACTN4-Va is designed and synthesized.

Likewise, for use in RT-PCR or Real-time PCR, primers are designed to amplify nucleotides covering the above mutation site(s) (i.e., nucleotides derived from exon 8').

Analysis of mRNA allows comprehensive detection of nucleotide substitutions based on, e.g., insertion of exon 8', i.e., a splice variant corresponding to the ACTN4 gene (SEQ ID NO: 1) shown in Accession No. NM_00004924.4.

Moreover, as for the determination of whether ACTN4 is mutated or whether a subject has a tumor, ACTN4 can be determined to be a mutated form if a desired band is detected or if a mutant nucleotide sequence is obtained as a result of probe hybridization, PCR-based amplification reaction or sequencing.

In this case, it is preferred to make a comparison with healthy person-derived mRNA expression levels. For example, the ratio of mRNA expression levels in a subject-derived sample (test value) to those in a healthy person-derived test sample (control value) is measured, and the subject may have cancer if such ratio is equal to or greater than the reference value.

In the method of the present invention, biological samples derived from multiple subjects may be used and measured for their levels of ACTN4-Va or mRNA thereof in some cases. Thus, a predetermined number of subjects (primary population) are measured for their levels of ACTN4-Va or mRNA thereof. The resulting measured values are used as master data and a comparison may be made between these master data and the levels of ACTN4-Va or mRNA thereof derived from individual subject-derived biological samples to be detected.

Further, if the subjects' data measured as above are equal to or greater than a predetermined value, these data may be incorporated into the values of the above population and subjected again to data processing (e.g., data averaging) of the levels of ACTN4-Va or mRNA thereof to increase the number of cases of target subjects (population). The increased number of cases can improve the accuracy of the critical value for the level of ACTN4-Va or mRNA thereof and optionally correct the critical value as appropriate to thereby improve the accuracy of detection or diagnosis of cancer.

Moreover, biological samples taken separately from subjects (e.g., patients or persons undergoing medical examinations) may be tested by the method of the present invention for detection of cancer in these subjects, e.g., before the actual treatment is started. Namely, mRNA is collected from each of the biological samples and tested for its level or nucleotide sequence. If the test result is positive or if the sample is analyzed to have a desired nucleotide sequence, a determination can be made that the subject has a high probability (risk) of developing cancer.

The above detection results may be used as main data or supplemental data for definitive diagnosis of cancer, by way of example. In more detail, for testing or definitive diagnosis of cancer, the above detection results may be combined with other test results, e.g., at least one selected from biopsy and other cancer marker levels to make a determination comprehensively.

4. Method for Cancer Evaluation

In the present invention, the detection results obtained by the detection method shown in Section 3 above can be used as an indicator to evaluate the state of cancer. A sample whose detection result is greater than the given reference value is defined to ACTN4-Va-positive, while a sample whose detection result is equal to or less than the given reference value is defined to ACTN4-Va-negative, and positive samples are determined to have a possibility of developing cancer and can be evaluated for the state of cancer. The given reference value may be set as appropriate, depending on the type of cancer.

The state of cancer is intended to mean the presence or absence of cancer or tumor occurrence or the progression of cancer or tumor, as exemplified by the presence or absence of cancerogenesis, the grade of malignancy of cancer, the presence or absence of cancer metastasis, the presence or absence of cancer recurrence and so on. For the above evaluation, these factors for the state of cancer may be selected either alone or in combination as appropriate. The presence or absence of cancer may be evaluated by determining whether or not a subject suffers from cancer. The grade of malignancy of cancer serves as an indicator representing how far the cancer has progressed, so that evaluation can be conducted for individual stages separately, or so-called early cancer and advanced cancer can be evaluated separately from each other. Cancer metastasis is evaluated by determining whether or not a neoplasm appears at a site away from the position of its primary focus. Cancer recurrence is evaluated by determining whether or not the cancer has appeared again after an intermission or remission.

5. Kit and Reagent Comprising the Antibody of the Present Invention

In the present invention, the antibody against ACTN4-Va can be used as a reagent or kit for ACTN4-Va detection. The reagent or kit of the present invention may be used for detection of tumors as mentioned above or other purposes.

When the antibody (e.g., monoclonal antibody) of the present invention is used as an agent for cancer detection or diagnosis, this monoclonal antibody may be formulated into a composition by being combined with other solvents or solutes. For example, distilled water, a pH-buffering reagent, a salt, a protein, a surfactant and so on may be combined for this purpose. Moreover, the monoclonal antibody may be enzymatically labeled before use. Examples of labeling enzymes available for use include HRP (horseradish peroxidase), as well as alkaline phosphatase, malate dehydrogenase, -glucosidase, -galactosidase, gold colloid and so on.

When the present invention is used for a kit, the kit may comprise, in addition to the antibody of the present invention, a solvent or a solute as mentioned above, a reagent for enzymatic labeling, antigen-immobilized microplates, an antibody diluent, OPD (orthophenylenediamine) tablets, a substrate solution, a reaction stop solution, a concentrated washing solution, manufacturer's instructions for use and so on. Moreover, the kit of the present invention may further comprise a reaction medium such as a buffer giving optimum conditions for the reaction, a buffer useful for stabilization of the reaction product, a stabilizing agent for the reactants, etc.

In the present invention, a probe and primers used for the detection of ACTN4-Va mRNA may be included in the reagent or kit of the present invention. The region based on which the probe or primers are designed is not limited in any way as long as exon 8' can be detected.

Sequencing primers have a length of 18 to 24 nucleotides, preferably 20 to 22 nucleotides. The nucleotide sequences of sequencing primers may be exemplified by the following sequences.

```
                                         (SEQ ID NO: 5)
        CCGTATAAGAACGTCAATGTGC (SEQ ID NO: 6)
        CTGGCCAGCTTCTCGTAGTC
```

Likewise, primers used to amplify the mRNA of ACTN4-Va by RT-PCR or real-time PCR are not limited in any way as long as exon 8' is amplified. Oligonucleotides having a length of 15 to 24 nucleotides, preferably 16 to 22 nucleotides, may be designed and synthesized from the upstream and downstream regions of exon 8' for use as primers.

For example, the nucleotide sequences of such primers may be exemplified by the following sequences.

```
        Forward:
                                         (SEQ ID NO: 7)
        TGGGCACTCTGAGGCCA Reverse:
                                         (SEQ ID NO: 8)
        CTTCTGAGCCCCCGAGAAA
```

Likewise, a probe used for hybridization (TaqMan probe) may be exemplified by the following sequence.

```
                                         (SEQ ID NO: 9)
        TGAGAAGGCCATCATG
```

Reagents and reaction conditions used for hybridization or PCR are well known to those skilled in the art.

6. Pharmaceutical Composition

The pharmaceutical composition of the present invention contains a substance inhibiting the functions of mutant α-actinin-4 (ACTN4-Va), preferably the antibody of the present invention, as an active ingredient and is effective for prevention or treatment of tumors.

Thus, the present invention provides a method for treating a tumor, which comprises administering a patient with a substance inhibiting the functions of mutant α-actinin-4.

The expression "substance inhibiting the functions of mutant α-actinin-4" is intended to mean a low molecular compound or a function-inhibiting antibody, and preferred are the antibody against ACTN4-Va according to the present invention and an inhibitory nucleic acid against a gene encoding ACTN4-Va.

Such an inhibitory nucleic acid against a gene encoding ACTN4-Va (which is also referred to as the ACTN4-Va gene) refers to a nucleic acid which suppresses the functions or expression of the gene, and examples include antisense nucleic acids, decoy nucleic acids, microRNAs, shRNAs or siRNAs, etc. These inhibitory nucleic acids are able to suppress the expression of the above gene and can be used as pharmaceutical compositions for tumor gene therapy.

<Antisense Nucleic Acid>

An antisense nucleic acid is a single-stranded nucleic acid sequence (either RNA or DNA) capable of binding to the mRNA (sense) or DNA (antisense) sequence of the ACTN4-Va gene (target gene). Such an antisense nucleic acid sequence has a length of at least 14 nucleotides, preferably 14 to 100 nucleotides. The antisense nucleic acid binds to the above gene sequence to form a duplex and thereby suppresses the transcription or translation of the ACTN4-Va gene.

The antisense nucleic acid may be prepared by chemical or biochemical synthesis procedures known in the art. For example, it is possible to use nucleic acid synthesis procedures using a DNA synthesizer, which is commonly used in gene recombination technology. The antisense nucleic acid is introduced into cells, for example, by various gene transfer techniques including DNA transfection or electroporation, or by using a virus vector.

<Decoy Nucleic Acid>

In the present invention, a decoy nucleic acid is intended to mean a short nucleic acid serving as a decoy that comprises a binding site for a transcription factor, and it is capable of binding to a transcription factor in the ACTN4-Va gene to thereby suppress promoter activity. When this nucleic acid is introduced into cells, a transcription factor will bind to this nucleic acid, so that the transcription factor will be competitively inhibited from binding to its genomic binding site and thus prevented from being expressed. More specifically, a decoy nucleic acid is a nucleic acid or an analog thereof, which is capable of binding to a target binding sequence. The decoy nucleic acid of the present invention may be designed as a single strand or as a double strand comprising its complementary strand on the basis of the promoter sequence for the above gene. The length of decoy nucleic acid may not be limited, but its length is 15 to 60 nucleotides, preferably 20 to 30 nucleotides.

The nucleic acid may be either DNA or RNA, or may comprise modified nucleic acids and/or pseudo nucleic acids therein. Alternatively, such a nucleic acid may be single-strand or double-strand, and may be cyclic or linear.

The decoy nucleic acid to be used in the present invention may be prepared by chemical or biochemical synthesis procedures known in the art. For example, it is possible to use nucleic acid synthesis procedures using a DNA synthesizer, which is commonly used in gene recombination technology. Alternatively, a nucleotide sequence serving as a template may be isolated or synthesized, followed by PCR or gene amplification using a cloning vector. Further, the nucleic acid thus obtained may be cleaved with a restriction enzyme or the like and ligated with DNA ligase to thereby prepare a desired nucleic acid. Furthermore, to obtain a decoy nucleic acid which is more stable within cells, bases and other moieties may be modified by chemical modifications such as alkylation, acylation, etc.

In the case of using a decoy nucleic acid, the promoter's transcriptional activity may be analyzed by using standard assays such as luciferase assay, gel shift assay, Western blotting, FACS analysis, RT-PCR, etc. Kits for these assays are also commercially available (e.g., Promega dual luciferase assay kit).

<RNA Interference>

In the present invention, synthetic small nucleic acid molecules capable of regulating gene expression in cells by RNA interference (RNAi), such as siRNA, microRNA (miRNA) and shRNA molecules, can be used.

In the case of using siRNA (small interfering RNA) molecules, various RNAs corresponding to the ACTN4-Va gene can be targeted. Such RNAs include mRNA, post-transcriptionally modified RNA of the ACTN4-Va gene, etc. Since the target gene in the present invention is a splice variant produced by selective splicing, siRNA molecules can be used to inhibit an exon segment (exon 8') from being expressed.

siRNA molecules may be designed on the basis of the criteria well known in the art. For example, as a target segment in the target mRNA, a segment covering 15 to 30 contiguous nucleotides, preferably 19 to 25 contiguous nucleotides, preferably starting with AA (most preferred), TA, GA or CA may be selected. siRNA molecules have a GC ratio of 30% to 70%, preferably 35% to 55%.

siRNA can be produced as a single-stranded hairpin RNA molecule folding on its own nucleic acid to form double-stranded portions. siRNA molecules may be obtained by standard chemical synthesis.

Preferred nucleotide sequences of siRNAs for use in the present invention are as shown below, by way of example.

```
                              (SEQ ID NO: 10)
       CCAUCAUGACUUACGUGUC (SEQ ID NO: 11)
       UUACGUGUCCUGCUUCUAC (SEQ ID NO: 12)
       AGAUGAGAAGGCCAUCAUG
```

In the present invention, shRNA may also be used for providing RNAi effect. shRNA is called short hairpin RNA, which has a stem-loop structure because some single-stranded regions form complementary strands with other regions.

shRNA may be designed to form a stem-loop structure as a part thereof. For example, assuming that a sequence covering a certain region is designated as sequence A, and a strand complementary to the sequence A is designated as sequence B, shRNA is designed to comprise the sequence A, a spacer and the sequence B linked in this order on a single RNA strand and to have an overall length of 45 to 60 nucleotides. Although the sequence A is a sequence covering a partial region of the target gene, there is no particular limitation on the target region and any region may be selected as a candidate for the target region. In addition, the sequence A has a length of 19 to 25 nucleotides, preferably 19 to 21 nucleotides.

Further, in the present invention, microRNA may be used to suppress expression of the above gene. microRNA (miRNA) is an intracellular single-stranded RNA molecule having a length of about 20 to 25 nucleotides and is a kind of ncRNA (non-coding RNA) which is considered to have the function of regulating the expression of other genes. miRNA is generated through processing upon transcription into RNA and is present as a nucleic acid capable of forming a hairpin structure which suppresses the expression of a target sequence.

Since miRNA is also among inhibitory nucleic acids based on RNAi, miRNA may also be designed and synthesized in the same manner as in the case of shRNA or siRNA.

Targets to be treated in the present invention are cancer patients, and the types of cancer are as shown above. Among them, preferred are neuroendocrine tumors, particularly lung primary high-grade neuroendocrine tumor (small cell lung cancer or large cell neuroendocrine carcinoma).

The antibody of the present invention or the inhibitory nucleic acid against the ACTN4-Va gene may be administered either alone or as a pharmaceutical composition together with a pharmaceutically acceptable carrier or diluent, etc. It may be given as a single dose or in divided doses.

As used herein, the term "pharmaceutically acceptable carrier" is intended to include excipients, diluents, extenders, disintegrants, stabilizers, preservatives, buffering agents, emulsifiers, flavorings, coloring agents, sweeteners, thickeners, correctives, solubilizers, or other additives, etc. One or more of these carriers can be used to prepare a pharmaceutical composition in the form of tablets, pills, powders, granules, injections, solutions, capsules, troches, elixirs, suspensions, emulsions or syrups, etc. Such a pharmaceutical composition may be administered orally or parenterally.

For oral administration, various excipients such as microcrystalline cellulose, sodium citrate, calcium carbonate, dipotassium phosphate, glycine and so on may be used in combination with a disintegrant, a binder, etc. Examples of a disintegrant include starch, alginic acid, a certain type of silicate double salt and so on, while examples of a binder include polyvinylpyrrolidone, sucrose, gelatin, gum arabic and so on. In addition, lubricants such as magnesium stearate, sodium lauryl sulfate, talc and so on are very effective for tablet formation. In the case of formulating an aqueous suspension or elixir for oral administration, an emulsifier and/or a suspending agent may optionally be used in combination with a diluent such as water, ethanol, propylene glycol, glycerine or any combination thereof.

Other dosage forms for parenteral administration include injections which comprise one or more active substances and are formulated in a standard manner.

In the case of injections, the antibody may be dissolved or suspended in a pharmaceutically acceptable carrier, e.g., physiological saline or commercially available injectable distilled water to give an antibody concentration of 5 mg/ml to 500 mg/ml. The injections thus prepared may be administered to human patients in need of treatment at a single dose of 250 mg/m$^2$ to 375 mg/m$^2$ per body surface area, preferably 250 mg/m$^2$ to 400 mg/m$^2$ per body surface area, given once a week and repeated several times.

However, the dose is not limited to this range and may vary depending on the body weight and symptoms of a patient and for each route of administration. The dose may also vary depending on differences in the drug susceptibility of patients to be treated, the way of drug formulation, the period of administration, and the interval of administration. Thus, a dose below the lower limit of the above range may be appropriate in some cases.

The mode of administration includes intravenous injection, subcutaneous injection, intracutaneous injection and so on, with intravenous injection being preferred. In some cases, injections may also be prepared as non-aqueous dilutions (e.g., propylene glycol, polyethylene glycol, vegetable oils such as olive oil, alcohols such as ethanol), suspensions or emulsions. Such injections may be sterilized by being filtered through a bacteria-retaining filter, being mixed with a disinfectant, or being irradiated. Injections may be prepared in reconstitutable form. Namely, injections may be converted into sterile solid or powder compositions by lyophilization or other techniques, and the resulting compositions may be dissolved in sterile injectable distilled water or other solvents before use.

For administration of siRNA, shRNA or miRNA, the effective amount is not limited in any way as long as it is enough to cause RNAi-mediated degradation of the target mRNA. Those skilled in the art would be able to determine the effective amount to be administered to patients in consideration of their body height and body weight, age, sex, the route of administration, or the way of administration, either topical or systemic, etc. For example, siRNA, shRNA or miRNA is administered to give an intracellular concentration of about 1 pM to about 20 pM, preferably 5 pM to 10 pM for parenteral administration (e.g., intravenous injection).

EXAMPLES

The present invention will be further described in more detail by way of the following examples and experimental examples, although the present invention is not limited to these examples and experimental examples.

Example 1

Preparation of Monoclonal Antibody Specific to ACTN4-Va (1) Preparation of Antigen ACTN4-Va is expressed only in small cell lung cancer patient tissues or small cell lung cancer-derived cell lines, or in testis among normal tissues. Moreover, when attempting to prepare an immunizing antigen from these tissues or cell lines, the desired antigen site is any of three amino acids derived from amino acid sequence substitutions present in a novel splice variant. Thus, for use as an antigen to obtain the desired antibody, a tissue- or cell-derived antigen protein comprising the full-length sequence is not suitable as an immunizing antigen. For this reason, an immunizing antigen comprising a sequence with amino acid substitutions (SEQ ID NO: 4) was chemically synthesized as a partial peptide.

Then, the synthesized ACTN4-Va partial peptide was used as an immunizing antigen.

The synthesized peptide and KLH serving as a carrier protein were linked via disulfide bonds by the MBS method to prepare an immunizing antigen.

(2) Immunization of Mice

Figure 1:
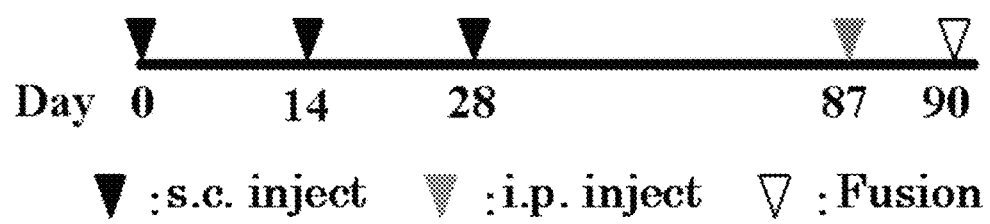
FIG. 1 shows a schematic view of immunization.
Figure 2A:
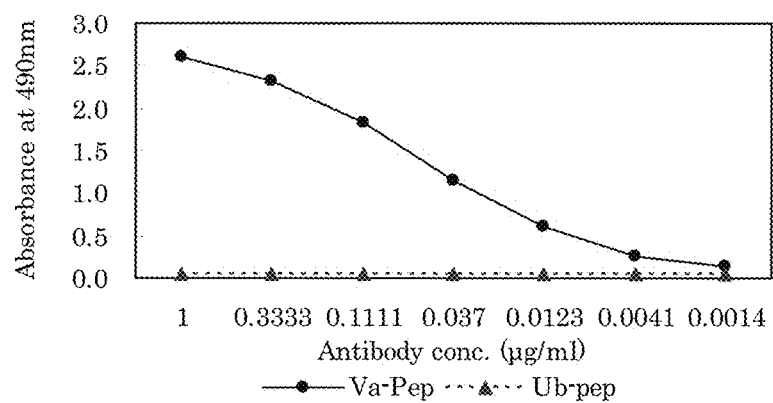
FIG. 2A shows the results of specificity verification testing for purified antibodies derived from clones "13G9" and "11H2.
Figure 2A:
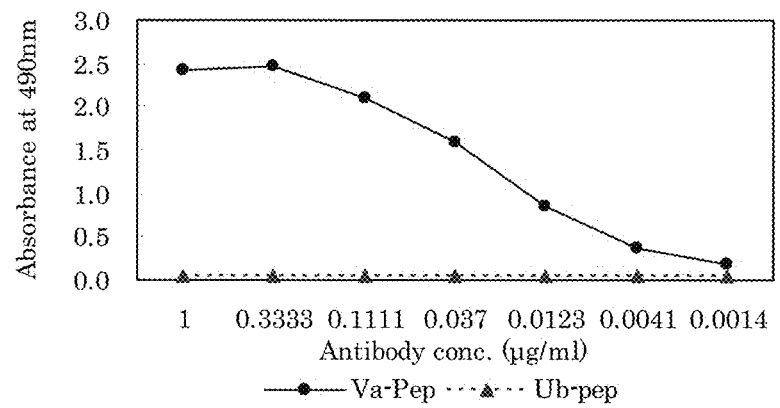
Figure 2B:
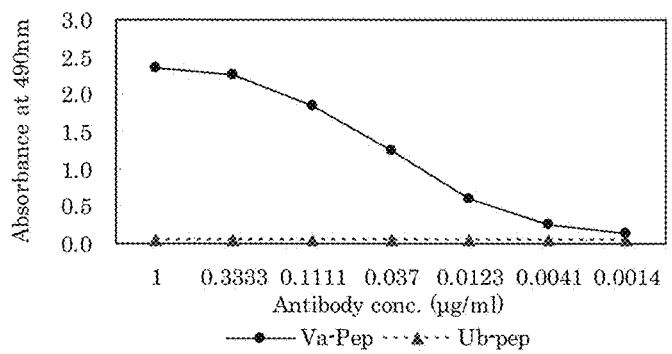
"
FIG. 2B shows the results of specificity verification testing for purified antibodies derived from clones "9B3," "15H2" and "10E10.
Figure 2B:
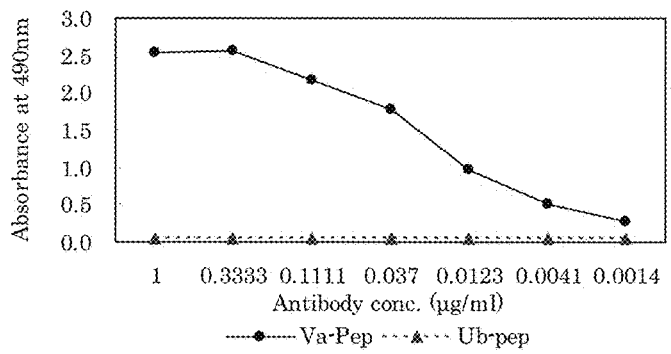
Figure 2B:
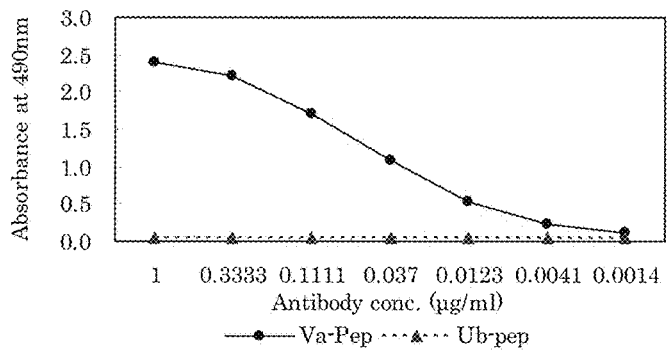

The overview of immunization is shown in FIG. 1. Immunization was accomplished in the following manner. The immunizing antigen prepared at 1.25 mg/mL was mixed with an equal amount of FCA to form an emulsion, which was then administered in 160 µL volumes under the dorsal skin of mice. Subsequently, the immunizing antigen at 1.25 mg/mL was mixed with an equal amount of FIA to form an emulsion, which was then administered in 80 µL volumes under the dorsal skin of the mice at intervals of 2 weeks. Ultimately, antigen administration was repeated five times in total, and the mice were confirmed for their antibody titers by ELISA. Mice found to have high antibody titers were finally administered with a mixture containing 40 μL of 1.25 mg/mL immunizing antigen and 460 μL of physiological saline via the intraperitoneal route, and after 3 days, their spleens were excised for cell fusion.

(3) Preparation of Spleen Cells and Cell Fusion

The excised spleens were each mashed to prepare spleen cells including ACTN4-Va antibody-producing cells, whereby about 1×10$^8$ spleen cells were able to be prepared per mouse. On the other hand, myeloma cells P3U1 were cultured and prepared to have a living cell rate of 95% or more on the day of cell fusion. These spleen cells and P3U1 cells were mixed at 5:1, followed by cell fusion in the presence of polyethylene glycol with a molecular weight of 1,450 at a concentration of 50%. After cell fusion, the cells were washed with the medium, suspended in HAT medium, and then seeded into each well of 96-well culture plates at 1×10$^5$ cells/well.

(4) Screening of Antibody Production-Positive Wells

After cell fusion, the culture supernatants at 10 days were collected and screened for antibody production-positive wells as described later in Experimental Example 1. Among 1264 wells, 31 wells were positive to ACTN4-Va and negative to ACTN4-Ub. The culture supernatants of these selected wells were screened again as described in Experimental Example 2, finally indicating that 17 wells were positive to ACTN4-Va.

(5) Cloning

The 17 wells highly specific to ACTN4-Va were cloned by limiting dilution. Namely, the cells were prepared at 5 cells/mL with 10% FCS-containing RPMI medium and added in a volume of 200 μL to each well of two 96-well culture plates. After 10 days, the culture supernatants were measured for their antibody titers and specificity for ACTN4-Va as described later in Experimental Examples 1 and 2 to confirm whether they were positive, thereby obtaining 5 clones derived from the respective wells. The respective established clones were designated as "13G9," "11H2," "9B3," "15H2" and "10E10."

Experimental Example 1

Procedures for Antibody Screening

50 μL of ACTN4-Va peptide prepared at 1 μg/mL with PBS (pH 7.0) was added to each well of 96-well microtiter plates as an immobilized antigen and allowed to stand at 25 C for 1 hour. Concurrently, for confirmation of specificity, 50 μL of ACTN4-Ub peptide DIVNTARPDEKAIMTYVSS (SEQ ID NO: 3) was also added and allowed to stand at 25 C for 1 hour. Then, after washing three times with 0.05% Tween 20-containing PBS (pH 7.0) (PBST), 200 μL of 0.5% gelatin-containing PBST (blocking solution) was added to each well and then allowed to stand at 25 C for 1 hour. After washing, 50 μL of undiluted culture supernatants were added to the respective wells and allowed to stand at 25 C for 1 hour. Then, after washing three times with PBST, 50 μL of HRP-labeled anti-mouse IgG antibody (KPL) diluted 2500-fold was added to each well and allowed to stand at 25 C for 1 hour. Then, after washing three times with PBST, 100 μL of an o-phenylenediamine solution prepared at 0.5 mg/mL with 0.02% hydrogen peroxide-containing 0.1 M citrate-phosphate buffer (pH 5.0) was added to each well and allowed to stand at 25 C for 10 minutes, followed by addition of 100 μL of a 1 M sulfuric acid solution to each well to thereby stop color development. Then, the absorbance at 490 nm was measured with an ELISA reader.

Experimental Example 2

Procedures for Western Blotting-Based Screening and Specificity Confirmation

SDS-polyacrylamide electrophoresis (hereinafter referred to as SDS-PAGE) was conducted in the following manner, followed by Western blotting (hereinafter referred to as WB) through semidry blotting to conduct confirmation testing for specificity.

In the case of using extracts derived from cancer cell lines, the following three cell extracts were used as samples for specificity evaluation: human small cell lung cancer-derived cancer cell line H69 specifically expressing ACTN4-Va, as well as non-expressing lines, i.e., human pancreatic adenocarcinoma-derived cell line BxPC-3 and human breast cancer-derived cell line MCF7. In the case of using extracts derived from expressing cells, the following four cell extracts were used in total as samples for specificity evaluation: two types of transformed cells, i.e., HEK293 GFP-ACTN4-Va (transformed with ACTN4-Va) and HEK293 GFP-ACTN4-Ub (transformed with ACTN4-Ub), as well as HEK293 and HEK293 GFP.

In addition, for the screening of culture supernatants, only H69 extracts were used for evaluation, while for confirmation testing with purified antibodies, cancer cell-derived or expressing cell-derived extracts were used for evaluation.

For sample preparation, 1×10$^7$ or more cells were provided for each case and mixed with 500 l or less of an extraction buffer containing 100-fold diluted protein inhibitor (Nacalai Tesque, Inc., Japan) in T-PER extraction buffer (Thermo), followed by extraction in accordance with the instruction manual to give a sample. Moreover, each sample was measured for its concentration by the BCA method (Thermo).

SDS-PAGE was accomplished by using a polyacrylamide gel of 10% uniform concentration (ATTO) and 1×SDS-PAGE running buffer for electrophoresis. Moreover, the samples were diluted with 6× sample buffer containing 9.3% DTT (dithiothreitol), treated by thermal reaction at 95° C. for 5 minutes, and then subjected to electrophoresis at 10 μg/lane. Electrophoresis conditions in this case were set at a constant current of 20 mA, and the electrophoresis was stopped at the time point where the line of bromophenol blue added for visualization purposes to the samples reached the bottom of the gel.

Next, WB was conducted. For pretreatment, 9×8.5 cm PVDF membrane (hereinafter referred to as the membrane) (Millipore Corporation) was treated with methanol for 1 minute and then immersed again in 20% methanol-containing blotting buffer before completion of the electrophoresis. Likewise, six filter papers precut to have the same size as the membrane were also immersed in the blotting buffer.

Next, blotting was performed on the membrane. On a semidry blotting system (GE; the former Amersham), three of the filter papers, the PVDF membrane, the SDS-PAGE gel containing the electrophoresed samples, and the remaining three filter papers were stacked in this order, followed by electrophoresis at a constant current for 50 minutes such that a terminal pressure of 15 V to 30 V was applied to the membrane at 1 cm$^2$/2 mA.

Next, blocking step was conducted. In the case of H69 samples, the lanes were blocked individually, or in the case of three types of samples including BxPC-3 and MCF7, the membrane was cut in groups of three types and then blocked by shaking reaction at 25° C. for 1 hour using N101 blocking buffer (NOF Corporation, Japan) diluted 3-fold with Milli-Q water.

Next, a primary reaction was conducted. For screening of culture supernatants, the culture supernatants were diluted 3-fold with a blocking solution diluted 10-fold in PBST (hereinafter referred to as the antibody diluent) before being reacted with the membrane. When confirming the specificity In addition, ACTN4-Va-positive rate was determined on the basis of the evaluation procedures shown in Experimental Example 3. In the result, the positive rate was 47.5% (58/122) in LCNEC and 60.0% (42/70) in SCLC, while the false positive rate was 0% in both Ad (0/158) and Sq (0/158). The positive rate in carcinoid, a kind of lung primary low-grade neuroendocrine tumor, was 9.8% (5/51) which was lower than the positive rate in the high-grade neuroendocrine tumors (Table 1).

TABLE 1

Frequency of expression of ACTN4 splice variant in pulmonary cancer

| | | Actinin-4 splice variant (%) | | | | | |
|---|---|---|---|---|---|---|---|
| | | Positive cases (%) | | | Negative cases (%) | | |
| | n | 3+ | 2+ | total | 1+ | 0 | total |
| Small cell carcinoma | 70 | 29 (41.4) | 13 (18.6) | 42 (60.0) | 20 (28.6) | 8 (11.4) | 28 (40.0) |
| Large-cell neuroendocrine tumor | 122 | 27 (22.1) | 31 (25.4) | 58 (47.5) | 41 (33.6) | 23 (18.9) | 64 (52.5) |
| Carcinoid | 51 | 0 (0) | 5 (9.8) | 5 (9.8) | 26 (51.0) | 20 (39.2) | 46 (90.2) |
| Adenocarcinoma | 156 | 0 (0) | 0 (0) | 0 (0) | 7 (4.5) | 149 (95.5) | 156 (100) |
| Squamous cell carcinoma | 158 | 0 (0) | 0 (0) | 0 (0) | 5 (3.2) | 155 (96.8) | 158 (100) | using purified antibodies, the purified antibodies were prepared at 1 µg/ml with the antibody diluent and then reacted with the membrane. Shaking reaction at 25° C. for 1 hour was conducted for each case.

Next, a secondary reaction was conducted. After the membrane was washed three times with PBST, HRP-labeled anti-mouse IgG antibody (IPL) was diluted 20000-fold with the antibody diluent, and then reacted with the membrane by shaking at 25° C. for 1 hour.

Next, chromogenic reaction was conducted. After the membrane was washed three times with PBST, chromogenic reaction was conducted by using Chemi-Lumi One (Nacalai Tesque, Inc., Japan) in accordance with the instruction manual. After said reaction, chemiluminescence was detected using a LAS-3000 (GE).

(6) Purification of Antibodies

From the 5 clones established in (5) above, desired monoclonal antibodies were purified in the following manner First, the established clones were suspended in a commercially available serum-free medium (Hybridoma SFM; Invitrogen) and prepared at $4 \times 10^5$ cells/mL. The cell suspensions (50 mL each) were introduced into T225 flasks and cultured at 37° C. under an environment of 5.0% $CO_2$ for about 1 week. After cultivation, the culture supernatants were collected. The collected culture supernatants were each applied to a Protein G column and eluted with glycine buffer (pH 3.0) to purify monoclonal antibodies.

Then, specificity confirmation test for ACTN4-Va was conducted again using the purified antibodies in the same manner as described in Experimental Examples 1 and 2.

Figure 3:
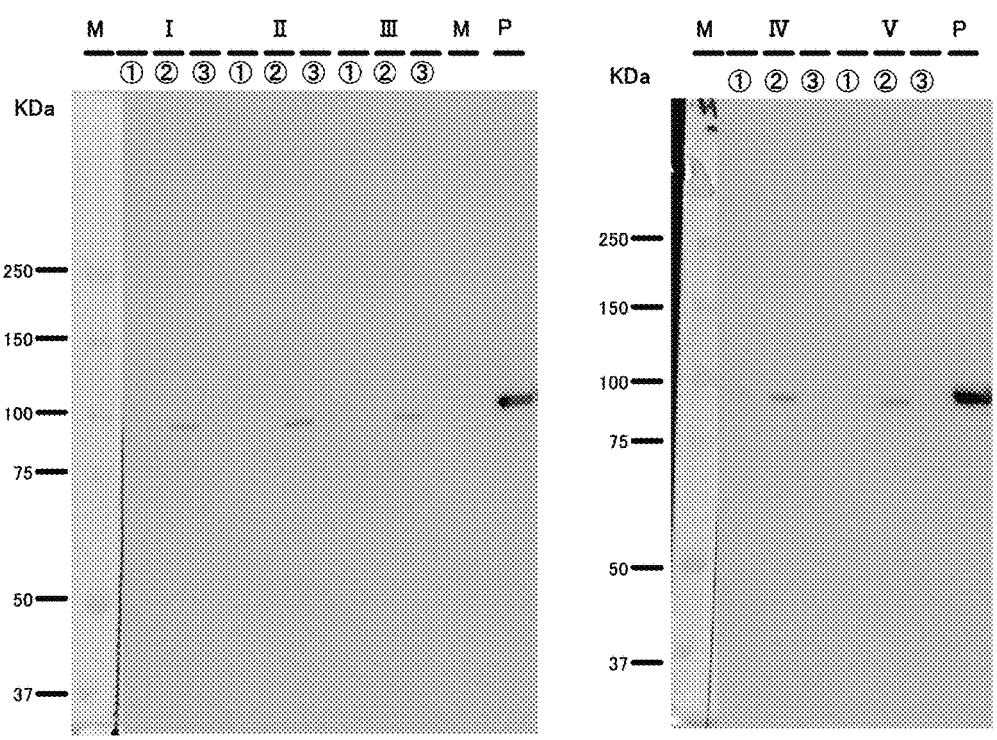
"
FIG. 3 shows the results of verification testing for specificity to ACTN4-Va using monoclonal antibodies derived from clones "13G9," "11H2," "9B3," "15H2" and "10E10," as determined by Western blotting.

As a result, the 5 clones obtained similar results to those of the culture supernatants (FIG. 2, FIG. 3 and FIG. 4).

(7) Diagnosis Compatibility Testing Based on Immunohistochemical Staining of Established Clones Diagnosis compatibility testing based on immunohistochemical staining with an antibody recognizing ACTN4-Va in living tissues was performed on the above 5 clones as described in Experimental Example 3 below. For diagnosis, excised pathological specimens (n=557) of lung primary HGNT, Ad and Sq were used. In the result, immunostaining in cancer tissues was achieved with the use of a specific monoclonal antibody "15H2" against ACTN4-Va (FIG. 5).

Table 1 shows the diagnostic results determined for positive rate in each cancer by immunohistochemical staining with a monoclonal antibody derived from the clone "15H2."

Experimental Example 3

Diagnosis Compatibility Testing Based on Immunohistochemical Staining

Immunostaining was conducted in the following manner to confirm diagnosis compatibility.

A tissue microarray (hereinafter referred to as TMA) prepared from the cases excised in the National Cancer Center Hospital and stored as formalin-fixed paraffin blocks was used as a sample.

TMA was prepared at a section thickness of 4 µm. A Ventana Discovery system (Roche) was used for automated immunostaining. TMA was deparaffinized in accordance with the program included in the Ventana Discovery system and then thermally treated to cause antigen activation, followed by inhibition of endogenous peroxidase activity.

Then, TMA was blocked with 2% pig serum (Vector Laboratories).

For primary reaction, anti-ACTN4-Va antibody was prepared at 5 µg/ml and allowed to hybridize at 37° C. for 60 minutes.

As a secondary antibody, biotinylated anti-mouse IgG (Vector Laboratories) was prepared by 100-fold dilution and allowed to hybridize at 37° C. for 30 minutes.

For chromogenic reaction, TMA was stained in accordance with the Ventana Discovery DAB kit protocol.

The subsequent evaluation of immunohistochemical staining was accomplished by two observers independently. A case showing strong expression all around the cell membrane was defined as (3+), a case showing strong granular expression in the cytoplasm was defined as (2+), a case showing weak staining in the cytoplasm was defined as (1+), and a case showing no staining was defined as (0). Among them, (3+) and (2+) cases were defined as positive, while (1+) and (0) cases were defined as negative.

(8) Overall Survival Rate Analysis Based on the Results of Immunohistological Diagnosis The results obtained in (7) were used to study the relationship between ACTN4-Va expression and prognosis in HGNT and its subclass tumors SCLC and LCNEC by Kaplan-Meier method and the Cox proportional hazard method. The overall survival period was analyzed by the Kaplan-Meier method, indicating that the survival period of ACTN4-Va-positive patients was significantly shorter than ACTN4-Va-negative patients in HGNT, SCLC and LCNEC (FIG. 6). The hazard ratio for death was evaluated by Cox proportional hazard method, indicating that ACTN4-Va expression would be able to serve as an independent factor for prognostic prediction in the respective cases of HGNT, SCLC and LCNEC (Table 2).

(2) Introduction into Cells siRNAs were each introduced into ACTN4-Va-expressing human lung small cell carcinoma cell line SBC-3 by using a cationic lipid for gene transfer.

SBC-3 was seeded at $3\times10^5$ cells/2 ml per well of 6-well culture plates and cultured for 24 hours in a $CO_2$ incubator.

Complexes used for introduction of the siRNAs were each prepared by reacting two mixtures. A first mixture was prepared by mixing 1 μl (10 pmol) of 10 μM each siRNA and 250 μl of Opti-MEM I (Invitrogen). A second mixture was prepared by mixing 5 μl of Lipofectamine 2000 (Invitrogen) and 250 μl of Opti-MEM I. These two mixtures were allowed to stand at room temperature for 20 minutes.

TABLE 2

Hazard ratios for death of patients with HGNT, SCLC, and LCNEC

| Factor | | n | Univariate analysis | | | Multivariate analysis | | |
|---|---|---|---|---|---|---|---|---|
| | | | Hazard retio | 95% confidence interval | p | Hazard retio | 95% confidence interval | p |
| HGNT | | | | | | | | |
| ACTN4 splice variant | Negative/positive | 90/90 | 2.2673 | 1.4265-3.6037 | 0.0005 | 2.0924 | 1.3122 3.3365 | 0.0019 |
| Age (year) | <65/≥65 | 78/111 | 1.0881 | 0.6985-1.6951 | 0.7089 | | | |
| Smoking | Absent/present | 7/182 | 1.4438 | 0.3548-5.8756 | 0.6080 | | | |
| Gender | Female/male | 35/154 | 1.3527 | 0.7327-2.4974 | 0.3342 | | | |
| Size | ≤3 cm/>3 cm | 100/89 | 1.4190 | 0.9168-2.1963 | 0.1164 | | | |
| Lymph node metastasis | Absent/present | 108/81 | 2.2122 | 1.4259-3.4321 | 0.0004 | 2.0368 | 1.3085 3.1704 | 0.0016 |
| Distant metastasis | Absent/present | 181/8 | 1.4219 | 0.5751-3.5156 | 0.4459 | | | |
| Histological subtype | LCNEC/SCLC | 120/69 | 1.3749 | 0.8818-2.1437 | 0.1601 | | | |
| SCLC | | | | | | | | |
| ACTN4 splice variant | Negative/positive | 27/42 | 2.4464 | 1.1016-5.4330 | 0.0280 | 2.3048 | 1.0293 5.1608 | 0.0420 |
| Age (year) | <65/≥65 | 27/42 | 0.9327 | 0.4657-1.8678 | 0.8440 | | | |
| Smoking | Absent/present | 5/64 | 1.2104 | 0.2893-5.0648 | 0.7937 | | | |
| Gender | Female/male | 20/49 | 1.9243 | 0.8344-4.4379 | 0.1247 | | | |
| Size | ≤3 cm/>3 cm | 47/22 | 0.7547 | 0.3503-1.6261 | 0.4724 | | | |
| Lymph node metastasis | Absent/present | 35/34 | 1.7328 | 0.8661-3.4667 | 0.1203 | | | |
| Distant metastasis | Absent/present | 67/2* | 5.6788 | 1.2925-24.9516 | 0.0215 | 4.2997 | 0.9659 19.1392 | 0.0560 |
| LCNEC | | | | | | | | |
| ACTN4 splice variant | Negative/positive | 63/57 | 2.0641 | 1.1554-3.6877 | 0.0144 | 1.9029 | 1.0615 3.4113 | 0.0310 |
| Age (year) | <65/≥65 | 51/59 | 1.1876 | 0.6675 2.1131 | 0.5586 | | | |
| Smoking* | Absent/present | 2/118* | — | — | — | | | |
| Gender | Female/male | 15/105 | 1.1263 | 0.4457-2.8465 | 0.8014 | | | |
| Size | ≤3 cm/>3 cm | 53/67 | 2.4024 | 1.2879-4.4812 | 0.0059 | 2.2114 | 1.1821 4.1370 | 0.0130 |
| Lymph node metastasis | Absent/present | 73/47 | 2.4678 | 1.3977-4.3571 | 0.0018 | 2.1129 | 1.1898 3.7521 | 0.0110 |
| Distant metastasis | Absent/present | 114/6 | 1.0482 | 0.3256-3.3749 | 0.9371 | | | |

*Hazard ratio could not calculate with Cox proportional hazard model.

Table 2 shows the results evaluated for hazard ratio for death of HGNT, SCLC and LCNEC patients upon ACTN4-Va expression by using the Cox proportional hazard method. In Table 2, ACTN4-Va protein expression is significant in multivariate analysis and therefore can be regarded as an independent prognostic factor for HGNT, SCLC and LCNEC.

Example 2

Inhibition of ACTN4-Va Expression by siRNA (1) Preparation of siRNAs siRNAs (SEQ ID NOs: 10, 11 and 12) preferred for use in the present invention were produced by chemical synthesis. The negative controls used were Silencer® Negative Control #1 siRNA and Silencer® Negative Control #2 siRNA (Ambion).

Likewise, for preparation of negative control mixtures, 10 μM negative control siRNAs were used in a volume of 0.5 μl (20 pmol).

Next, the complexes (500 μl each) were added to the wells where SBC-3 was cultured, followed by culturing at 37° C. for 72 hours in a $CO_2$ incubator.

(3) Western Blotting

Extracts of SBC-3 after the introduction reaction were provided for Western blotting to detect ACTN4-Va with the purified antibody 15H2.

(4) Results

The results obtained are shown in FIG. 7. In FIG. 7, the respective lanes represent bands obtained with the following siRNAs or controls.

Lane 1:

(SEQ ID NO: 10)
CCAUCAUGACUUACGUGUC

-continued

Lane 2:

(SEQ ID NO: 11)

UUACGUGUCCUGCUUCUAC

Lane 3:

(SEQ ID NO: 12)

AGAUGAGAAGGCCAUCAUG

Lane 4:
negative control (Silencer ® Negative Control #1 siRNA)

Lane 5:
negative control (Silencer ® Negative Control #2 siRNA)

The band of ACTN4-Va was absent in Lanes 1 to 3, indicating that ACTN4-Va expression can be suppressed by using the siRNAs of the present invention. Thus, the siRNAs of the present invention are useful for oncotherapy, particularly for neuroendocrine tumor treatment.

INDUSTRIAL APPLICABILITY

The antibody of the present invention allows highly sensitive and specific detection of ACTN4-Va in specimens such as tissues, cells and blood; and hence it is useful for detection and diagnosis of tumors, preferably cancers, or is useful as an antitumor pharmaceutical composition.

SEQUENCE LISTING FREE TEXT

SEQ ID NO: 5: synthetic DNA
SEQ ID NO: 6: synthetic DNA
SEQ ID NO: 7: synthetic DNA
SEQ ID NO: 8: synthetic DNA
SEQ ID NO: 9: synthetic DNA
SEQ ID NO: 10: synthetic RNA
SEQ ID NO: 11: synthetic RNA
SEQ ID NO: 12: synthetic RNA

The invention claimed is:

1. An antibody against mutant α-actinin-4 comprising an amino acid sequence with at least one amino acid residue substitution in the region between positions 245 and 263 in the amino acid sequence of α-actinin-4, wherein the antibody recognizes all or a part of the substituted amino acid residue(s) in the region and does not bind to constitutively expressed α-actinin-4, wherein the amino acid sequence with substituted amino acid residue(s) is represented by DIVGTLRPDEKAIMTYVSC (SEQ ID NO: 4).

2. The antibody according to claim 1, wherein the antibody is a monoclonal antibody.

3. The antibody according to claim 2, which is produced by a hybridoma having Accession No. NITE BP-1140.

4. An antibody binding to an epitope, to which the antibody according to claim 2 binds.

5. The antibody according to claim 2, wherein the antibody is a chimeric antibody, a humanized antibody or a reconstituted human antibody.

6. A fragment of the antibody according to claim 1.

7. A hybridoma producing the antibody according to claim 2.

8. A hybridoma having Accession No. NITE BP-1140.

9. A method for preparing an antibody against mutant α-actinin-4 which does not bind to constitutively expressed α-actinin-4, which comprises the steps of:

(a) immunizing a non-human mammal with a partial peptide comprising the amino acid sequence of the region between positions 245 and 263 in the amino acid sequence of α-actinin-4, wherein the partial peptide has at least one amino acid residue substitution in said region;

(b) collecting the antibody from the non-human mammal; and (c) selecting an antibody which binds an amino acid sequence with at least one amino acid residue substitution in the region between positions 245 and 263 in the amino acid sequence of α-actinin-4, wherein the antibody recognizes all or a part of the substituted amino acid residue(s) in the region and does not bind to constitutively expressed α-actinin-4.

10. A method for preparing a monoclonal antibody against mutant α-actinin-4 which does not bind to constitutively expressed α-actinin-4, which comprises the steps of:
(a) immunizing a non-human mammal with a partial peptide comprising the amino acid sequence of the regionbeetween positions 245 and 263 in the amino acid sequence of α-actinin-4, wherein the partial peptide has at least one amino acid residue substitution in said region;
(b) collecting antibody-producing cells from the immunized non-human mammal of step (a);
(c) allowing the antibody-producing cells obtained in step (b) to be fused with myeloma cells;
(d) collecting the antibody from the fusion cells obtained in step (c); and
(e) selecting an antibody which binds an amino acid sequence with at least one amino acid residue substitution in the region between positions 245 and 263 in the amino acid sequence of α-actinin-4, wherein the antibody recognizes all or a part of the substituted amino acid residue(s) in the region and does not bind to constitutively expressed α-actinin-4.

11. The method according to claim 9, wherein the non-human mammal is a GANP transgenic non-human mammal.

12. A method for detecting mutant α-actinin-4, which is characterized by reacting the antibody according to claim 1 or an antigen-binding fragment thereof with a biological sample to thereby detect mutant α-actinin-4.

13. A reagent for tumor detection or diagnosis, which comprises the antibody according to claim 1 or a fragment thereof.

14. The reagent according to claim 13, wherein the tumor is lung primary high-grade neuroendocrine tumor.

15. An antitumor pharmaceutical composition, which comprises a substance inhibiting the functions of mutant α-actinin-4 comprising an amino acid sequence with at least one amino acid residue substitution in the region between position 245 and 263 in the amino acid sequence of α-actinin-4, wherein the substance inhibiting the functions of mutant α-actinin-4 is the antibody according to claim 1 or a fragment thereof.

16. An antitumor pharmaceutical composition, which comprises a substance inhibiting the functions of mutant α-actinin-4 comprising an amino acid sequence with at least one amino acid residue substitution in the region between position 245 and 263 in the amino acid sequence of α-actinin-4, wherein the substance inhibiting the functions of mutant α-actinin-4 is the antibody according to claim 1 or a fragment thereof.

17. The pharmaceutical composition according to claim 15, wherein the tumor is lung primary high-grade neuroendocrine tumor.

* * * * *